(12) United States Patent
Kozbor

(10) Patent No.: US 9,296,803 B2
(45) Date of Patent: Mar. 29, 2016

(54) METHODS AND COMPOSITIONS CONTAINING FC FUSION PROTEINS FOR ENHANCING IMMUNE RESPONSES

(75) Inventor: Danuta Kozbor, Buffalo, NY (US)

(73) Assignee: Health Research, Inc., Buffalo, NY (US)

( * ) Notice: Subject to any disclaimer, the term of this patent is extended or adjusted under 35 U.S.C. 154(b) by 190 days.

(21) Appl. No.: 13/577,990

(22) PCT Filed: Mar. 11, 2011

(86) PCT No.: PCT/US2011/028070
§ 371 (c)(1),
(2), (4) Date: Sep. 18, 2012

(87) PCT Pub. No.: WO2011/112915
PCT Pub. Date: Sep. 15, 2011

(65) Prior Publication Data
US 2013/0011436 A1  Jan. 10, 2013

Related U.S. Application Data

(60) Provisional application No. 61/312,982, filed on Mar. 11, 2010.

(51) Int. Cl.
*A61K 48/00* (2006.01)
*C07K 14/52* (2006.01)
*A61K 39/00* (2006.01)

(52) U.S. Cl.
CPC ............ *C07K 14/521* (2013.01); *A61K 39/0011* (2013.01); *A61K 2039/505* (2013.01); *A61K 2039/572* (2013.01); *C07K 2319/30* (2013.01)

(58) Field of Classification Search
None
See application file for complete search history.

(56) References Cited

U.S. PATENT DOCUMENTS

| 2004/0258677 A1 | 12/2004 | Waldmann et al. |
| 2005/0002939 A1 | 1/2005 | Zlotnik et al. |
| 2005/0100551 A1 | 5/2005 | Zielinski et al. |
| 2005/0164935 A1 | 7/2005 | Clark-Lewis et al. |
| 2005/0164936 A1 | 7/2005 | Clark-Lewis et al. |

FOREIGN PATENT DOCUMENTS

| JP | 2009527460 | 7/2009 |
| WO | WO 0183525 A2 * | 11/2001 |
| WO | 2008142303 | 1/2009 |
| WO | 2009022215 | 5/2010 |

OTHER PUBLICATIONS

Gil, M., et al., Targeting a Mimotope Vaccine to Activating Fcgamma Receptors Empowers Dendritic Cells to Prime Specific CD8+ T Cell Responses in Tumor-Bearing Mice, J. Immunol., Nov. 15, 2009, vol. 183, No. 10, pp. 6808-6818.
Bolesta, E., et al., DNA Vaccine Expressing the Mimotope of GD2 Ganglioside Induces Protective GD2 Cross-reactive Antibody Responses, Cancer Res., Apr. 15, 2005, vol. 65, No. 8, pp. 3410-3418.
McCart, J. A. et al., Systemic cancer therapy with a tumor-selctive vaccinia virus mutant lacking thymidine kinase and vaccinia growth factor genes, Cancer Research, Dec. 15, 2001, vol. 61, pp. 8751-8757.
Huang, Eugene H. et al. A CXCR4 Antagonist CTCE-9908 Inhibits Primary Tumor Growth and Metastasis of Breast Cancer, Journal of Surgical Research, Aug. 1, 2009, vol. 155, No. 2, pp. 231-236.
Gil, Margaret et al. Targeting CXCL12/CXCR4 Singnaling with Oncolytic Virotherapy Disrupts Tumor Vasculature and INhibits Breast Cancer Metastases, PNAS, Mar. 18, 2013, vol. 110, No. 14, pp. E1291-E1300.

* cited by examiner

*Primary Examiner* — Amy Juedes
(74) *Attorney, Agent, or Firm* — Hodgson Russ LLP

(57) ABSTRACT

Provided are compositions and methods for inhibiting cell growth. The cells that are targeted by the compositions and methods of the invention express an antigen, a mimotope of the antigen, or a CXCR4 chemokine receptor. The method entails administering to an individual a polynucleotide encoding an immunoglobulin Fc and an antigen expressed by the cells or a mimotope of the antigen. The method also involves administering to the individual a composition which contains a polynucleotide encoding an immunoglobulin Fc and an antagonist peptide of a CXCR4 chemokine receptor expressed by the cells. Also provided are proteins encoded by the polynucleotides.

4 Claims, 10 Drawing Sheets

Figure 1

A. Induction of antitumor immune responses with 47-LDA- or 47-LDA-Fcγ2a-DCs

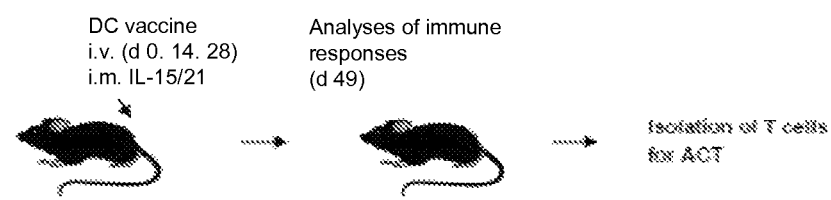

DC vaccine i.v. (d 0, 14, 28) i.m. IL-15/21 → Analyses of immune responses (d 49) → Isolation of T cells for ACT

B. Inhibition of NXS2 tumor growth by ACT and DC vaccines

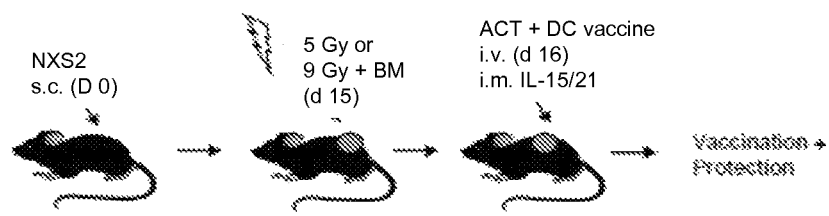

NXS2 s.c. (D 0) → 5 Gy or 9 Gy + BM (d 15) → ACT + DC vaccine i.v. (d 16) i.m. IL-15/21 → Vaccination + Protection

C. Inhibition of metastatic disease by ACT and DC vaccines

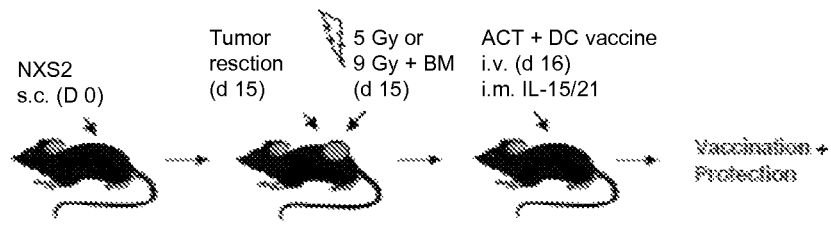

NXS2 s.c. (D 0) → Tumor resection (d 15) → 5 Gy or 9 Gy + BM (d 15) → ACT + DC vaccine i.v. (d 16) i.m. IL-15/21 → Vaccination + Protection Figure 5
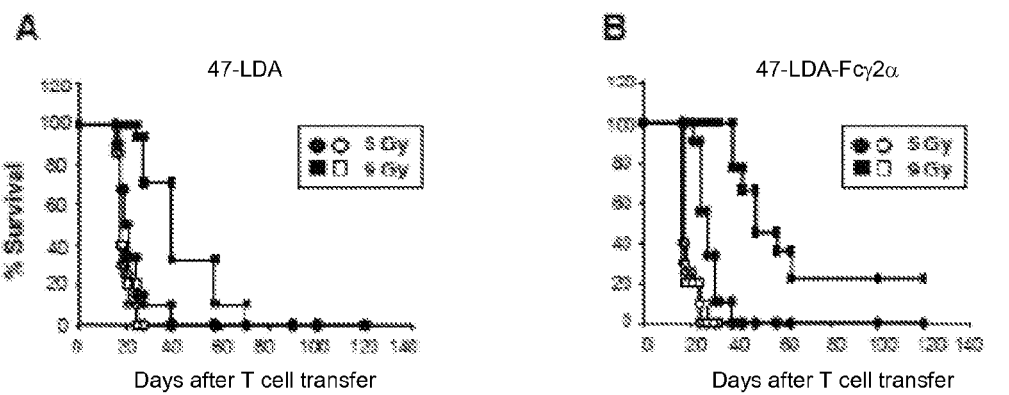
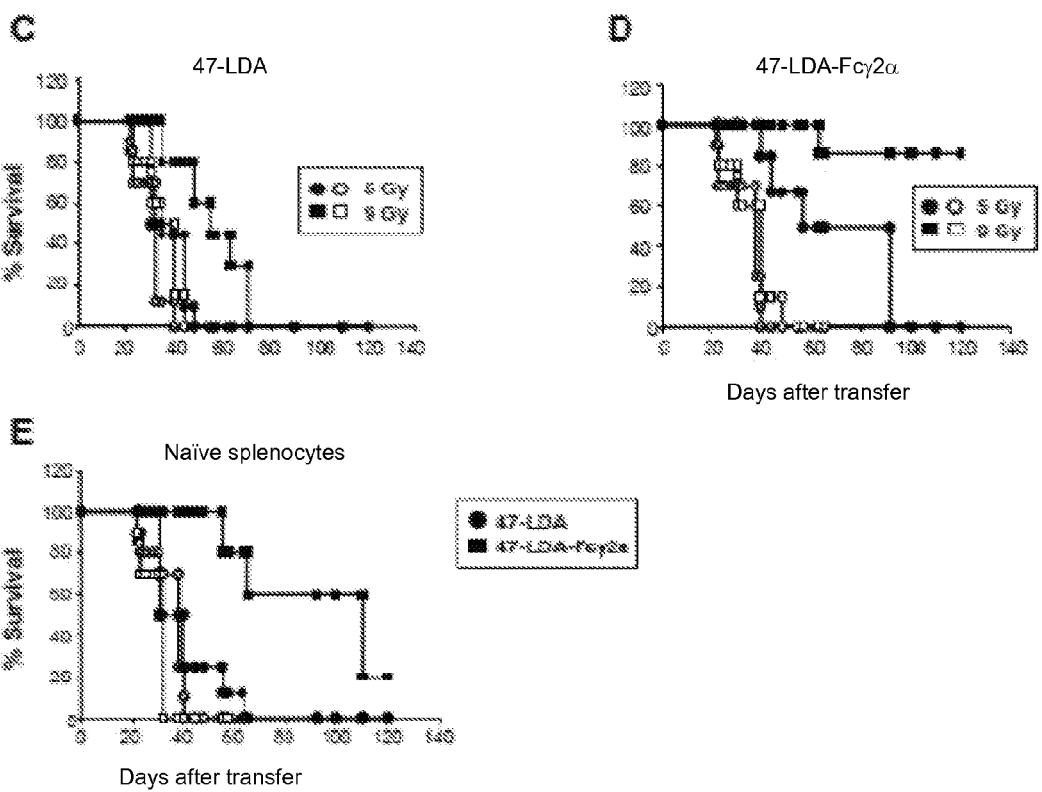

Figure 6
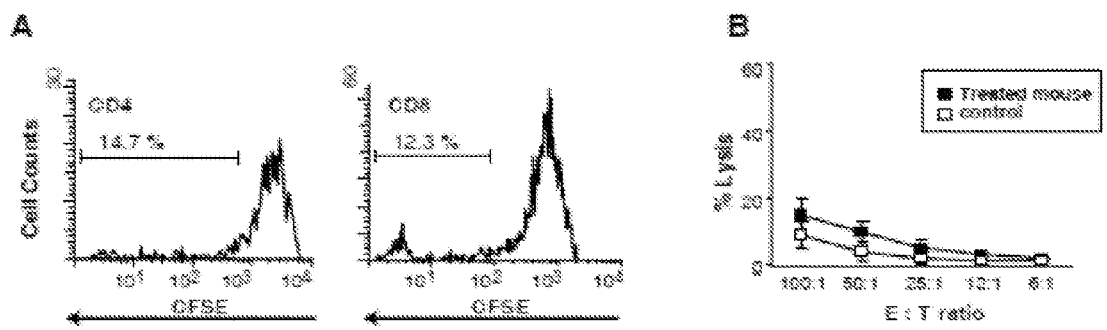
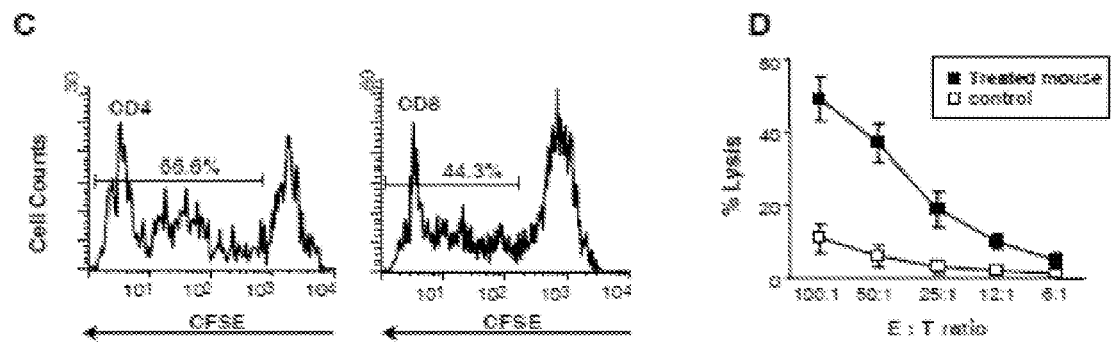

SEQUENCE LISTING

```
<160> NUMBER OF SEQ ID NOS: 8

<210> SEQ ID NO 1
<211> LENGTH: 20
<212> TYPE: PRT
<213> ORGANISM: artificial sequence
<220> FEATURE:
<223> OTHER INFORMATION: LDA mimotope amino acid sequence

<400> SEQUENCE: 1
```

```
Gly Pro Gly Pro Gly Glu Asp Pro Ser His Ser Leu Gly Leu Asp Ala
1               5                   10                  15

Ala Leu Phe Met
            20

<210> SEQ ID NO 2
<211> LENGTH: 64
<212> TYPE: PRT
<213> ORGANISM: artificial sequence
<220> FEATURE:
<223> OTHER INFORMATION: LDA-mimotope fused with immunoglobulin Fc and T
      helper epitopes

<400> SEQUENCE: 2

Lys Cys Lys Arg Gln Cys Gly Pro Gly Pro Gly Ala Lys Phe Val Ala
1               5                   10                  15

Ala Trp Thr Leu Lys Ala Ala Ala Gly Pro Gly Pro Gly Cys Lys Arg
            20                  25                  30

Lys Ile His Ile Gly Pro Gly Gln Ala Phe Tyr Thr Gly Pro Gly Pro
        35                  40                  45

Gly Glu Asp Pro Ser His Ser Leu Gly Leu Asp Ala Ala Leu Phe Met
    50                  55                  60

<210> SEQ ID NO 3
<211> LENGTH: 13
<212> TYPE: PRT
<213> ORGANISM: artificial sequence
<220> FEATURE:
<223> OTHER INFORMATION: 13 amino acid nonnatural pan DR epitope (PADRE)

<400> SEQUENCE: 3

Ala Lys Phe Val Ala Ala Trp Thr Leu Lys Ala Ala Ala
1               5                   10

<210> SEQ ID NO 4
<211> LENGTH: 15
<212> TYPE: PRT
<213> ORGANISM: HIV

<400> SEQUENCE: 4

Cys Lys Arg Lys Ile His Ile Gly Pro Gly Gln Ala Phe Tyr Thr
1               5                   10                  15

<210> SEQ ID NO 5
<211> LENGTH: 17
<212> TYPE: PRT
<213> ORGANISM: artificial sequence
<220> FEATURE:
<223> OTHER INFORMATION: peptide CXCR4 chemokine receptor antagonist

<400> SEQUENCE: 5

Lys Gly Val Ser Leu Ser Tyr Arg Lys Arg Tyr Ser Leu Ser Val Gly
1               5                   10                  15

Lys

<210> SEQ ID NO 6
<211> LENGTH: 8
<212> TYPE: PRT
<213> ORGANISM: artificial sequence
<220> FEATURE:
<223> OTHER INFORMATION: portion of CTCE-9908

<400> SEQUENCE: 6

Lys Gly Val Ser Leu Ser Tyr Arg
```

<210> SEQ ID NO 7
<211> LENGTH: 330
<212> TYPE: PRT
<213> ORGANISM: human

<400> SEQUENCE: 7

```
Ala Ser Thr Lys Gly Pro Ser Val Phe Pro Leu Ala Pro Ser Ser Lys
1               5                   10                  15
Ser Thr Ser Gly Gly Thr Ala Ala Leu Gly Cys Leu Val Lys Asp Tyr
            20                  25                  30
Phe Pro Glu Pro Val Thr Val Ser Trp Asn Ser Gly Ala Leu Thr Ser
        35                  40                  45
Gly Val His Thr Phe Pro Ala Val Leu Gln Ser Ser Gly Leu Tyr Ser
    50                  55                  60
Leu Ser Ser Val Val Thr Val Pro Ser Ser Leu Gly Thr Gln Thr
65                  70                  75                  80
Tyr Ile Cys Asn Val Asn His Lys Pro Ser Asn Thr Lys Val Asp Lys
                85                  90                  95
Lys Val Glu Pro Lys Ser Cys Asp Lys Thr His Thr Cys Pro Pro Cys
            100                 105                 110
Pro Ala Pro Glu Leu Leu Gly Gly Pro Ser Val Phe Leu Phe Pro Pro
        115                 120                 125
Lys Pro Lys Asp Thr Leu Met Ile Ser Arg Thr Pro Glu Val Thr Cys
    130                 135                 140
Val Val Val Asp Val Ser His Glu Asp Pro Glu Val Lys Phe Asn Trp
145                 150                 155                 160
Tyr Val Asp Gly Val Glu Val His Asn Ala Lys Thr Lys Pro Arg Glu
                165                 170                 175
Glu Gln Tyr Asn Ser Thr Tyr Arg Val Val Ser Val Leu Thr Val Leu
            180                 185                 190
His Gln Asp Trp Leu Asn Gly Lys Glu Tyr Lys Cys Lys Val Ser Asn
        195                 200                 205
Lys Ala Leu Pro Ala Pro Ile Glu Lys Thr Ile Ser Lys Ala Lys Gly
    210                 215                 220
Gln Pro Arg Glu Pro Gln Val Tyr Thr Leu Pro Pro Ser Arg Asp Glu
225                 230                 235                 240
Leu Thr Lys Asn Gln Val Ser Leu Thr Cys Leu Val Lys Gly Phe Tyr
                245                 250                 255
Pro Ser Asp Ile Ala Val Glu Trp Glu Ser Asn Gly Gln Pro Glu Asn
            260                 265                 270
Asn Tyr Lys Thr Thr Pro Pro Val Leu Asp Ser Asp Gly Ser Phe Phe
        275                 280                 285
Leu Tyr Ser Lys Leu Thr Val Asp Lys Ser Arg Trp Gln Gln Gly Asn
    290                 295                 300
Val Phe Ser Cys Ser Val Met His Glu Ala Leu His Asn His Tyr Thr
305                 310                 315                 320
Gln Lys Ser Leu Ser Leu Ser Pro Gly Lys
                325                 330
```

<210> SEQ ID NO 8
<211> LENGTH: 377
<212> TYPE: PRT
<213> ORGANISM: human

<400> SEQUENCE: 8

```
Ala Ser Thr Lys Gly Pro Ser Val Phe Pro Leu Ala Pro Cys Ser Arg
 1               5                  10                  15

Ser Thr Ser Gly Gly Thr Ala Ala Leu Gly Cys Leu Val Lys Asp Tyr
            20                  25                  30

Phe Pro Glu Pro Val Thr Val Ser Trp Asn Ser Gly Ala Leu Thr Ser
        35                  40                  45

Gly Val His Thr Phe Pro Ala Val Leu Gln Ser Ser Gly Leu Tyr Ser
    50                  55                  60

Leu Ser Ser Val Val Thr Val Pro Ser Ser Ser Leu Gly Thr Gln Thr
65                  70                  75                  80

Tyr Thr Cys Asn Val Asn His Lys Pro Ser Asn Thr Lys Val Asp Lys
                85                  90                  95

Arg Val Glu Leu Lys Thr Pro Leu Gly Asp Thr Thr His Thr Cys Pro
            100                 105                 110

Arg Cys Pro Glu Pro Lys Ser Cys Asp Thr Pro Pro Pro Cys Pro Arg
        115                 120                 125

Cys Pro Glu Pro Lys Ser Cys Asp Thr Pro Pro Pro Cys Pro Arg Cys
    130                 135                 140

Pro Glu Pro Lys Ser Cys Asp Thr Pro Pro Pro Cys Pro Arg Cys Pro
145                 150                 155                 160

Ala Pro Glu Leu Leu Gly Gly Pro Ser Val Phe Leu Phe Pro Pro Lys
                165                 170                 175

Pro Lys Asp Thr Leu Met Ile Ser Arg Thr Pro Glu Val Thr Cys Val
            180                 185                 190

Val Val Asp Val Ser His Glu Asp Pro Glu Val Gln Phe Lys Trp Tyr
        195                 200                 205

Val Asp Gly Val Glu Val His Asn Ala Lys Thr Lys Pro Arg Glu Glu
    210                 215                 220

Gln Tyr Asn Ser Thr Phe Arg Val Val Ser Val Leu Thr Val Leu His
225                 230                 235                 240

Gln Asp Trp Leu Asn Gly Lys Glu Tyr Lys Cys Lys Val Ser Asn Lys
                245                 250                 255

Ala Leu Pro Ala Pro Ile Glu Lys Thr Ile Ser Lys Thr Lys Gly Gln
            260                 265                 270

Pro Arg Glu Pro Gln Val Tyr Thr Leu Pro Pro Ser Arg Glu Glu Met
        275                 280                 285

Thr Lys Asn Gln Val Ser Leu Thr Cys Leu Val Lys Gly Phe Tyr Pro
    290                 295                 300

Ser Asp Ile Ala Val Glu Trp Glu Ser Ser Gly Gln Pro Glu Asn Asn
305                 310                 315                 320

Tyr Asn Thr Thr Pro Pro Met Leu Asp Ser Asp Gly Ser Phe Phe Leu
                325                 330                 335

Tyr Ser Lys Leu Thr Val Asp Lys Ser Arg Trp Gln Gln Gly Asn Ile
            340                 345                 350

Phe Ser Cys Ser Val Met His Glu Ala Leu His Asn Arg Phe Thr Gln
        355                 360                 365

Lys Ser Leu Ser Leu Ser Pro Gly Lys
    370                 375
```

METHODS AND COMPOSITIONS CONTAINING FC FUSION PROTEINS FOR ENHANCING IMMUNE RESPONSES

CROSS-REFERENCE TO RELATED APPLICATIONS

This application claims priority to U.S. application No. 61/312,982, filed Mar. 11, 2010, the disclosure of which is incorporated herein by reference.

STATEMENT REGARDING FEDERALLY SPONSORED RESEARCH

This invention was made with government support under grant no. R21EB008071 awarded by the National Institutes of Health. The government has certain rights in the invention.

FIELD OF THE INVENTION

The present invention relates generally to modulating immune responses and more specifically to enhancing cell-mediated immune response in an individual using Fc fusion proteins.

BACKGROUND OF THE INVENTION

The successful application of cancer vaccines to treat patients has remained elusive, and there is an ongoing and unmet need for improving the efficacy of compositions and methods that stimulate cell mediated and other immune response against antigens that are expressed by cancer cells. The present invention meets these and other related needs.

SUMMARY OF THE INVENTION

The present invention provides compositions and methods for inhibiting growth of cells in an individual. The cells that are targeted by the compositions and methods of the invention express an antigen, a mimotope of the antigen, or a CXCR4 chemokine receptor.

In one embodiment, the method comprises administering to the individual a composition comprising a polynucleotide encoding an immunoglobulin (Ig) Fc and an antigen expressed by the cells or a mimotope of the antigen. In another embodiment, the method comprises administering to the individual a composition comprising a polynucleotide encoding an immunoglobulin Fc and an antagonist peptide of a CXCR4 chemokine receptor expressed by the cells. In various embodiments, the invention inhibits the growth of cancer cells, which can be but are not necessarily limited to tumor cells.

The polynucleotide which encodes the Ig Fc is in one embodiment a recombinant oncolytic vaccinia virus.

The fusion proteins encoded by the polynucleotides can comprise a human IgG1 Fc or human IgG3 Fc, and can further comprise T helper epitopes. The invention also provides compositions comprising polynucleotides encoding the proteins, and/or the encoded proteins. The proteins comprise an immunoglobulin Fc and an antigen or a peptide mimic of the antigen, or an immunoglobulin Fc and an antagonist peptide of a receptor expressed by cancer cells.

BRIEF DESCRIPTION OF THE FIGURES

FIG. 1. Schematic representation of vaccination with 47-LDA- or 47-LDA-Fcγ2a-pulsed dendritic cells (DCs) and adoptive cell transfer (ACT) in tumor-bearing mice. A, Vaccination with 47-LDA- or 47-LDA-Fcγ2a-pulsed DCs. A/J mice (n=5) were immunized in a 2-week interval with 47-LDA- or 47-LDA-Fcγ2a-pulsed DCs in the presence of IL-15 and IL-21 vectors. Three weeks after the third immunization CD8$^+$ splenocytes were obtained by negative selection and used for the ACT in NXS2-bearing mice. B, Inhibition of primary tumor growth by ACT and DC vaccines. A/J mice were challenged with $2\times10^6$ NXS2 cells. Fifteen days later, lymphopenia in the tumor-bearing mice was induced by 5 Gy TBI or 9 Gy TBI plus BM transfer ($10^7$ cells) one day prior to the ACT and DC vaccination. Adoptive transfer of antigen-experienced CD8$^+$ T cells ($2\times10^7$) together with the DC vaccine was delivered on day 16. Tumor growth was monitored by measuring s.c. tumors once to thrice a week with a microcaliper and determining tumor volume (width×length×width/2=mm$^3$). C, Inhibition of metastatic disease by ACT and DC vaccine. NXS2-bearing mice underwent non-myeloablative or myeloablative TBI at the time of tumor excision. One day later, the mice received ACT of CD8$^+$ T cells ($2\times10^7$) from the immunized mice or unseparated splenocytes from naïve mice together with the DC vaccine. Survival was defined as the point at which mice were sacrificed due to extensive tumor growth or development of metastases.

FIG. 5 Inhibition of NXS2 primary and metastatic tumor growth by 47-LDA- and 47-LDA-Fcγ2a-DC vaccines and ACT. Upper panel, protection against primary tumor growth by ACT and 47-LDA-DC vaccine (A) and 47-LDA-Fcγ2a-DC vaccines (B). A/J mice (n=8-10) were injected s.c. with $2\times10^6$ NXS2 cells and treated 15 days later with i.v. adoptive transfer of $CD8^+$-enriched splenocytes isolated from 47-LDA- or 47-LDA-Fcγ2a-vaccinated syngeneic mice. Lymphopenia of tumor-bearing mice was induced by TBI (5 Gy; ●) or (9 Gy; ■) plus BM ($10^7$ cells) transplantation one day before $CD8^+$ T cell transfer as described in the Materials and Methods section. Mice were immunized in a 2-week interval with the DC vaccines in the presence of IL-15 and IL-21 vectors. NXS2 tumor-bearing mice that were irradiated with 5 Gy (○) or 9 Gy (□) plus BM transplant served as controls. Lower panel, Control of metastatic disease by adoptively transferred $CD8^+$ splenocytes and 47-LDA-DC (C) and 47-LDA-Fcγ2a-DC (D) vaccines. For the immunotherapy of disseminated disease, NXS2-bearing A/J mice that underwent nonmyeloablative (5 Gy; ●) or myeloablative (9 Gy; ■) TBI at the time of tumor excision received ACT of $CD8^+$ splenocytes ($2\times10^7$ cells) from the immunized mice together with 47-LDA- or 47-LDA-Fcγ2a-DC vaccine. NXS2-challenged mice that were irradiated with 5 Gy (○) or 9 Gy (□) plus BM transplant served as controls. E, NXS2-challenged mice received ACT from naïve A/J mice together with the DC vaccines. Mice were immunized in a 2-week interval with the DC vaccine in the presence of IL-15 and IL-21 vectors. The control mice had the primary tumor excised with (○) or without (□) TBI and BM transplantation. Survival was defined as the point at which mice were sacrificed due to extensive tumor growth. Kaplan-Meier survival plots were prepared, and significance was determined using logrank Mantel-Cox method.

FIG. 6. Analyses of cellular responses in tumor-bearing and tumor-free mice after ACT and DC vaccination. Upper panel, Lack of proliferative responses (A) and CTL activity (B) in splenocytes of NXS2-bearing mice. A, Splenocytes isolated from mice that developed progressively growing tumor after ACT of naïve splenocytes and 47-LDA polypeptide-DC vaccine were loaded with CFSE and cultured with 47-LDA-expressing syngeneic DCs (ratio 20:1) for 72 h. Cells were stained with PE-conjugated anti-CD4 or anti-CD8 mAbs and analyzed by flow cytometry. The percentage of cells that underwent more than one round of cell division is indicated. Data are from one representative experiment of four performed. B, CTL activities of stimulated or control $CD8^+$ splenocytes from tumor-bearing mice against NXS2 cells were analyzed in a standard $^{51}$Cr-release assay. All determinations were made in triplicate samples, and results are presented as the means±SD of three independent experiments. Lower panel, Analyses of proliferative responses (C) and CTL activities against NXS2 (D) in tumor-free mice after receiving ACT from naïve mice and 47-LDA-Fcγ2a-DC vaccine. Experiments were carried out as described in the upper panel.

DESCRIPTION OF THE INVENTION

Figure 2:
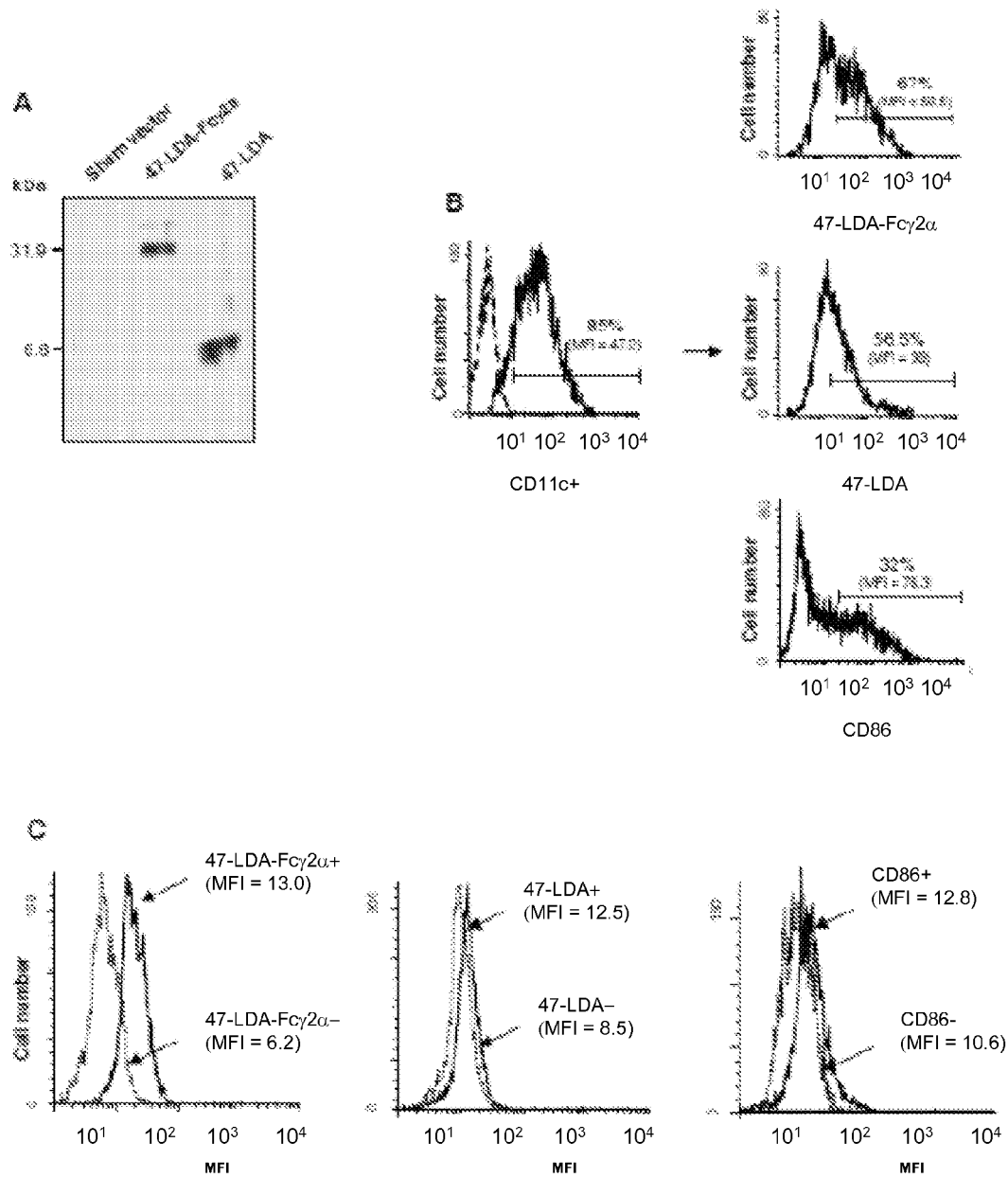
FIG. 2. Characterization of the 47-LDA-Fcγ2a fusion protein and its interaction with DCs. A, Western blotting of 47-LDA-Fcγ2a fusion protein and 47-LDA polypeptide with biotinylated 14G2a mAb and streptavidin-HRP. B, Binding of 47-LDA-Fcγ2a fusion protein and 47-LDA polypeptide to immature CD11c$^+$ DCs. Bone-marrow (BM)-derived DCs were stained with FITC-conjugated CD11c-specific mAb in combination with biotinylated 47-LDA-Fcγ2a fusion protein or 47-LDA polypeptide followed by streptavidin-PE and analyzed by flow cytometry. DCs stained with anti-CD86-PE mAb were included as a specificity control. The percent and mean fluorescent intensity (MFI) of 47-LDA-Fcγ2a, 47-LDA, and CD86 molecules on CD11c-positive DCs are given. Arrows indicate the source of cells in the histograms. Data are from one representative experiment of three performed. C, Intracellular expression of IL-12p70 by 47-LDA-Fcγ2a$^+$, 47-LDA$^+$, CD86$^+$ DCs and their negative counterparts after LPS stimulation. Immature DCs were stained with biotinylated 47-LDA-Fcγ2a fusion protein, 47-LDA polypeptide or CD86-specific mAb followed by streptavidin-PE. The positive and negative populations were sorted on BD FACSAria™ flow cytometer, incubated overnight with 1 μg/mlLPS and analyzed for IL-12p70 expression by intracellular staining with rat anti-mouse IL-12p70 mAb, specific for the IL-12p35 subunit, followed by goat anti-rat secondary antibody. Background staining (MFI<2.6) was assessed using an isotype control Ab. All flow cytometric evaluations were performed on FACScan or FACSCalibur flow cytometer. After gating on forward and side scatter parameters, at least 10,000-gated events were routinely acquired and analyzed using CellQuest software. Data are from one representative experiment of three performed.

The present invention takes advantage of our discovery that a fusion protein comprising an Fc region of an antibody and i) a mimotope that mimics an epitope that is present in an antigen; or ii) a peptide antagonist of a receptor expressed on cancer cells, can be used to enhance the immune response to cells that express the antigen and inhibit the signaling through the receptor to which the peptide antagonist binds. The invention includes compositions comprising such fusion proteins, compositions comprising polynucleotides encoding such fusion proteins, and methods of using such compositions for prophylaxis and/or therapy of disease. The method comprises administering a composition of the invention to an individual such that the growth of cells that express the antigen or cells that express the receptor to which the peptide antagonist binds is inhibited.

As used herein a "mimotope" means a peptide sequence that mimics the structure of an epitope. An immune response raised against the mimotope will be directed to the epitope it mimics, and thus will also recognize an antigen comprising the epitope. In one embodiment, it is considered that the mimotope itself can function as an antigen.

We demonstrate that therapeutic vaccines comprising fusion proteins that contain an activating Fc fusion protein and either a mimotope or a peptide antagonist of a receptor expressed on cancer cells generate anti-tumor responses which are characterized in part by stimulation of antigen-specific T cells.

In a particular demonstration of the invention, we show that therapeutic vaccines with a CD166 cross-reactive mimotope of GD2 ganglioside (referred to herein as "47-LDA") expressed in the context of the activating Fc fusion protein generated tumor-specific T cells in tumor-bearing syngeneic mice. The mimotope was expressed as a fusion protein in conjunction with universal T helper epitopes and the murine IgG2a Fc fragment (47-LDA-Fcγ2a) to deliver the antigenic cassette to the activating Fcγ receptors on dendritic cells (DCs).

The sequence of the 47-LDA mimotope is GPGPGEDP-SHSLGLDAALFM (SEQ ID NO:1). An exemplary amino acid sequence comprising universal T helper epitopes and the 47-LDA mimotope is provided in SEQ ID NO:2, which is:

KCKRQCGPGPGAKFVAAWTLKAAAGPG-PGCKRKIHIGPGQAFYTGPG PGEDPSH-SLGLDAALFM. The amino acids in positions 1-6 of SEQ ID NO:2 constitute a spacer. The amino acids in positions 7-11 and 25-29 constitute linkers. While it is considered that any T helper epitopes can be used in connection with the invention, non-limiting embodiments of suitable T helper epitopes include the universal Th peptide referred to as nonnatural pan DR epitope (PADRE) [AKFVAAWTLKAAA SEQ ID NO:3 and the V3 loop of the HIV gp120 glycoprotein [CKRKIHIG-PGQAFYT SEQ ID NO:4). Each of these representative T helper epitopes are also shown in SEQ ID NO:X.

We also showed that immunization of tumor-bearing mice with the 47-LDA-Fcγ2a fusion protein induced higher levels of antitumor immune responses and protection than a 47-LDA polypeptide-dendritic cell (DC) vaccine. The antitumor efficacy of the therapeutic 47-LDA-Fcγ2a-DC vaccine was comparable to that achieved by a virotherapy-associated cancer vaccine using a recombinant oncolytic vaccinia virus (rOVV) expressing the 47-LDA-Fcγ2a fusion protein. The latter treatment however did not require total body irradiation (TBI) or adoptive cell transfer (ACT) and resulted in induction of antitumor immune responses in the setting of established tolerance.

In another embodiment of the invention we employ an anticancer agent (CTCE-9908) that is a CXCR4 chemokine receptor antagonist. This peptide antagonist of CXCR4 comprises the amino acid sequence: KGVSLSYR-K-RYSLS-VGK (SEQ ID NO:5). Thus, in one embodiment, the peptide antagonist of CXCR4 comprises the sequence KGVSLSYR (SEQ ID NO:6).

CTCE-9908 blocks the interaction of the CXCR4 receptor with CXCL12, which is critical in the infiltration of organ tissue by metastatic cells, thereby reducing tumor metastasis. CXCR4 receptors are expressed on many tumor cell types.

The CTCE-9908 peptide has been developed by Chemokine Therapeutics, Vancouver, Canada and been used in Phase I/II clinical trials in late stage cancer patients. By performing the method of the invention, we take advantage of the Fc fragments naturally present disulfide bonds to preserve the dimeric structure of the CTCE-9908 peptide. We expressed the CTCE-9908 peptide in the context of the activating murine and human Fcγ fragments (IgG2a and IgG1, respectively) in DNA vectors and demonstrate antitumor efficacy of the construct in murine syngeneic (T41 breast carcinoma) and xenograft (FADU human head and neck carcinoma) models with the murine version of the CTCE-fusion protein. We believe this augments the therapeutic efficacy of the peptide by mobilizing Antibody-Dependent Cell-Mediated Cytotoxicity (ADCC) tumor-killing mechanism. Thus, the present invention provides various compositions and methods for enhancing an immune response to an antigen, wherein the antigen is presented as a fusion construct in combination with the Fc region of an immunoglobulin (Ig) that preferentially binds with the activating Fcγ receptors. Accordingly, in one embodiment the invention provides a composition comprising a fusion construct, wherein the fusion construct comprises an Fc region of a murine IgG2a or human IgG1 or a fragment of such Fc regions. In various embodiments, the Fc region is an Fc region or fragments thereof that is from an IgA, IgG, or IgE antibody, although Fc regions from other antibody types, or synthetic/artificial Fc regions can also be used. The Fc region can comprise or consist of an amino acid sequence that is identical to an Fc region produced by a mammal, such as a human. In various embodiments, the Fc region may have between 80% to 100% (including all integers there between) amino acid sequence similarity to an Fc region produced by a mouse and/or a human. The Fc region may be an intact Fc region, meaning an entire Fc region, or may be a fragment of the Fc region. Fragments of the Fc region preferably comprise amino acid sequences that specifically bind to Fcγ receptors. Those skilled in the art will recognize that the "Fc region" of an antibody means the "Fragment, crystallizable" region of the antibody, which comprises two heavy chains that contribute two or three constant domains (CD) depending on the class of the antibody. Nucleotide sequences encoding Fc regions, as well as the amino acid sequences of Fc regions for mouse and human immunoglobulins are well known in the art. In one embodiment, a suitable human Ig gamma-1 C region, Homo sapiens, for use as the Ig region in the instant invention has the sequence ASTKGPSVFP LAPSSKSTSG GTAALGCLVK DYFPEPVTVS WNSGALTSGV HTFPAVLQSSGLYSLSSVVT VPSSSLGTQT YICNVNHKPS NTKVDKKVEP KSCDKTHTCP PCPAPELLGGPSVFLFPPKP KDTLMISRTP EVTCVVVDVS HEDPEVKFNW YVDGVEVHNA KTKPREEQYN STYRVVSVLT VLHQDWLNGK EYKCKVSNKA LPAPIEKTIS KAKGQPREPQ VYTLPPSRDE LTKNQVSLTC LVKGFYPSDI AVEWESNGQP ENNYKTTPPV LDSDGSFFLY SKLTVDKSRW QQGNVFSCSV MHEALHNHYT QKSLSLSPGK (SEQ ID NO:7).

In another embodiment, a suitable human Ig gamma-3 chain C region has the ASTKGPSVFP LAPCSRSTSG GTAALGCLVK DYFPEPVTVS WNSGALTSGV HTFPAVLQSS GLYSLSSVVT VPSSSLGTQT YTCNVNHKPS NTKVDKRVEL KTPLGDTTHT CPRCPEPKSC DTPPPCPRCP EPKSCDTPPP CPRCPEPKSC DTPPPCPRCP APELLGGPSV FLFPPKPKDT LMISRTPEVT CVVVDVSHED PEVQFKWYVD GVEVHNAKTK PREEQYNSTF RVVSVLTVLH QDWLNGKEYK CKVSNKALPA PIEKTISKTK GQPREPQVYT LPPSREEMTK NQVSLTCLVK GFYPSDIAVE WESSGQPENN YNTTPPMLDS DGSFFLYSKL TVDKSRWQQG NIFSCSVMHE ALHNRFTQKS LSLSPGK (SEQ ID NO:8).

Because individual antibody isotypes possess different affinities for Fcγreceptors (with activating Fcγ receptors having higher affinities for murine IgG2a and IgG2b isotypes or human IgG1 and IgG3 isotypes), differences in the ratios of activating-to-inhibitory receptor binding by the presented antigenic complex may predict the ability of DCs to induce immune responses. Harnessing this pathway may allow the recruitment of adaptive immunity and immunologic memory by antibody therapy or cancer vaccines.

In one embodiment, the Fc portion of the fusion proteins comprises only antibody heavy chain(s).

Those skilled in the art will recognize that for demonstration of the invention using murine animal models, the Fc portion of the fusion protein is preferably an IgG2a or IgG2b Fc murine Ig portion, while for therapy and/or prophylaxis of disease in humans, the Fc portion is preferably an IgG1 or an IgG3 Fc portion.

In certain embodiments, the Fc portion of the fusion proteins provided herein do not include antigen recognition portions (i.e., the antibody portion of the fusion proteins do not contain antibody variable regions). Thus, the fusion proteins are distinct from antibodies that do contain antigen binding portions, and which may also include cross-linked or otherwise connected mimotopes, antigens, or peptide receptor ligands.

DNA constructs encoding the Fc-fusion proteins can be made using any conventional techniques well known to those skilled in the art. For example, the Fc-fusion encoding constructs can be made using commercially available reagents. For instance, INVIVOGEN offers the pFUSE-Fc family of plasmids developed to facilitate the construction of Fc-Fusion proteins by fusing a sequence encoding a given protein to the Fc region of an immunoglobulin (Ig). In this construct, the Fc region comprises the CH2 and CH3 domains of the IgG heavy chain and the hinge region. The hinge acts as a flexible spacer between the two parts of the Fc-fusion protein, which permits each part of the fusion protein to function independently. In general, any Fc region (and accordingly any polynucleotides encoding such Fc region) that activates Fcγ receptors can be used in performance of the invention.

The DNA constructs encoding the fusion proteins can be expressed to produce the fusion proteins for isolation and/or purification, or for therapeutic purposes, using any suitable protein expression system. Various tags or other moieties can be added to the fusion proteins so that they can be readily purified using, for example, various affinity chromatography methods.

For therapeutic purposes, compositions such as pharmaceutical preparations comprising the fusion proteins, and/or comprising polynucleotides encoding the fusion proteins, can be prepared. Compositions for use in therapeutic purposes may be prepared by mixing the Fc-fusion proteins and/or polynucleotides encoding them with any suitable pharmaceutically acceptable carriers, excipients and/or stabilizers. Some examples of compositions suitable for mixing with the agent can be found in: *Remington: The Science and Practice of Pharmacy* (2005) 21st Edition, Philadelphia, Pa. Lippincott Williams & Wilkins. The compositions may further comprise any suitable adjuvant.

If the therapeutic agent used in the method of the invention is a polynucleotide, it can be administered to the individual as a naked polynucleotide, in combination with a delivery reagent, or as a recombinant plasmid or viral vector which comprises and/or expresses the polynucleotide agent. Suitable delivery reagents for administration include the Minis Transit TKO lipophilic reagent; lipofectin; lipofectamine; cellfectin; or polycations (e.g., polylysine), or liposomes. In one embodiment, the Fc-Ag/antagonist fusion is encoded by a recombinant oncolytic recombinant vaccinia virus (rOVV). In this regard, oncolytic viruses replicate in and destroy cancer cells selectively. This primary mechanism of action is complemented by secondary mechanisms including expression of immunogenic/therapeutic proteins by the virus at the site of cytolysis. Although the vast majority of clinical trials to evaluate the activity of oncolytic viruses have used local (e.g., intratumoral) or regional (e.g., intracavitary or intra-arterial) routes, it is considered that effective treatment of invasive and metastatic cancer will be preferably performed using systemic administration of the virus [See, for example Hu, J. C., et al. Clin Cancer Res 2006. 12: 6737-6747].

Poxviruses are characterized by their ability to travel systemically through the blood because the extracellular enveloped vaccinia virus shrouds itself in a host cell-derived envelope that contains several host complement control proteins and few exposed viral proteins making it resistant to neutralization by complement. Engineered oncolytic vaccinia virus (OVV) has demonstrated promising results in the treatment of cancer in preclinical models and early clinical trials [Kirn, D. H. and Thorne, S. H., *Nat Rev Cancer* 2009. 9: 64-71, Mastrangelo, M. J., et al. Cancer Gene Ther 1999. 6: 409-422; Park, B. H., et al. Lancet Oncol 2008. 9: 533-542; Thorne, S. H., et al. Curr Gene Ther 2005. 5: 429-443; Zeh, H. J. and Bartlett, D. L., Cancer Gene Ther 2002. 9: 1001-1012; Zhu, J., et al. Blood 2007. 109: 619-625], and systemic virus spread has been demonstrated in patients with widespread metastases [Park, B. H., et al. Lancet Oncol 2008. 9: 533-542, 47-49; Mastrangelo, M. J., et al J Clin Invest 2000. 105: 1031-1034; Mastrangelo, M. J., et al. Adv Exp Med Biol 2000. 465: 391-400; DiPaola, R. S., et al. J Transl Med 2006. 4: 1]. However, most patients have not been effectively treated, and thus the efficacy of OVV in humans is expected to benefit from combination with the compositions and methods provided by the present invention.

In one embodiment, the polynucleotide is administered to the individual via administration of antigen presenting cells, such as dendritic cells, which comprise a polynucleotide that expresses the Fc-Ag/antagonist fusion protein. "Fc-Ag/antagonist" means the Fc region is present in a chimeric protein with either an antigen, a mimotope thereof, or a cancer-cell specific peptide receptor antagonist, or nucleotide sequence encoding such a chimeric protein(s). In one embodiment, the Fc-Ag/antagonist can be expressed as a fusion protein in conjunction with universal T helper epitopes and the Fc fragment to deliver the antigenic cassette to the activating Fcγ receptors on the antigen presenting cells for induction of antigen specific T cells.

In another embodiment, the invention provides a method for enhancing an immune response to an antigen comprising adoptively transferring T cells expanded by the Fc-Ag fusion protein-dendritic cells to the individual. In one embodiment, the adoptively transferred T cells are CD8+ T cells. "CD8+" T cells means T cells that express CD8 (cluster of differentiation 8). CD8 is a well characterized transmembrane glycoprotein that serves as a co-receptor for T cell receptors (TCR). CD8 binds to the Class I major histocompatibility complex (MHC-I) protein on the surface of antigen presenting cells in humans. In one embodiment, the invention provides an adoptive transfer of isolated population of vaccine-induced CD8+ T cells and the Fc-Ag fusion protein-expressing dendritic cells to a tumor-bearing host to facilitate expansion of the adoptively transferred T cells in vivo and inhibition of tumor growth, or a polynucleotide encoding the Fc-Ag fusion.

In one embodiment, the invention elicits an enhanced T cell response against the antigen that is present (or mimicked by) the antigen in the Fc-Ag fusion of the invention. The enhanced T cell response can include but is not necessarily limited to an increase in T cells that exhibit cytotoxic activity against cells that bear the antigen, or T cells that exhibit enhanced sustenance and/or antigen-recall responses to the antigen, or an increase of the amount and/or activity of effector T cells that are specific for the antigen, or combinations of the foregoing types of cell mediated immune responses. The T cell response elicited by the method of the invention may be accompanied by beneficial changes in humoral and/or innate immune responses. In one embodiment, an enhanced immune response can be evidenced by an inhibition of the growth of tumor cells that express the antigen in the individual, and/or by a prolongation of the survival of the individual.

It is expected that any antigen comprising an epitope(s) that can be mimicked by a peptide (a mimotope) is suitable for use in the present invention. It is preferred that the antigen comprises an epitope that is suitable for presentation by antigen presenting cells in conjunction with MHC class I molecules. Thus, the antigen may be or may comprise a protein or a peptide when it is present in the fusion protein. The antigen may be a recombinant antigen, it may be chemically synthesized, it may be isolated from a cell culture, or it may be isolated from a biological sample obtained from an individual. The antigen may be present on cells in an infectious organisms or the antigen may be expressed by a diseased or infected cell, tissue or organ.

In one embodiment, the antigen is a tumor antigen. Tumor antigens can be commercially available antigens, or they can be obtained by conventional techniques, such as by recombinant methods, or by preparation of tumor cell lysates to identify novel antigens for use in the compositions and methods of the invention.

In various embodiments, the cancer cell antigen may be expressed by cancer cells, specific examples of which include but are not limited to fibrosarcoma, myxosarcoma, liposarcoma, chondrosarcoma, osteogenic sarcoma, chordoma, angiosarcoma, endotheliosarcoma, lymphangiosarcoma, pseudomyxoma peritonei, lymphangioendotheliosarcoma, synovioma, mesothelioma, Ewing's tumor, leiomyosarcoma, rhabdomyosarcoma, colon carcinoma, pancreatic cancer, breast cancer, ovarian cancer, prostate cancer, squamous cell carcinoma, basal cell carcinoma, adenocarcinoma, head and neck cancer, sweat gland carcinoma, sebaceous gland carcinoma, papillary carcinoma, papillary adenocarcinomas, cystadenocarcinoma, medullary carcinoma, bronchogenic carcinoma, renal cell carcinoma, hepatoma, bile duct carcinoma, choriocarcinoma, seminoma, embryonal carcinoma, Wilns' tumor, cervical cancer, testicular tumor, lung carcinoma, small cell lung carcinoma, bladder carcinoma, epithelial carcinoma, glioma, astrocytoma, medulloblastoma, craniopharyngioma, ependymoma, pinealoma, hemangioblastoma, acoustic neuroma, oliodendroglioma, meningioma, melanoma, neuroblastoma, retinoblastoma, leukemia, lymphoma, multiple myeloma, thymoma, Waldenstrom's macroglobulinemia, and heavy chain disease.

In one embodiment, the antigen is a CD166 cross-reactive mimotope of the GD2 ganglioside. In another embodiment, the antigen is the CTCE-9908.

The antigen may be an antigen that is expressed by an infectious agent or infectious organism, non-limiting examples of which include viruses, bacteria, fungi, protozoans, or any other parasite or otherwise infectious agent.

Those skilled in the art will recognize how to formulate dosing regimens for performing the method of the invention, taking into account such factors as the molecular makeup of the antigen, the size and age of the individual to be treated, and the type and stage of a disease with which the individual may be suspected of having or may have been diagnosed with. The invention may be used to elicit an enhanced immune response that is prophylactic or therapeutic. The individual to whom the composition is administered can be an individual in need of the treatment, and/or an individual who has been diagnosed with, is suspected of having, or is at risk for developing a disease or other disorder that is associated with expression of the antigen.

The amount of Fc-Ag/antagonist fusion protein, or expression vector encoding the Fc-Ag/antagonist protein, or cells, such as antigen presenting cells comprising the Fc-Ag/antagonist fusion protein or an expression vector or other expression cassette encoding the Fc-Ag/antagonist fusion, to be included in a composition of the invention and/or to be used in the method of the invention can be determined by those skilled in the art, given the benefit of the present disclosure. Thus, in one embodiment, an effective amount of a composition of the invention is administered. An effective amount can be an amount of the composition that inhibits growth of cells in the individual that express the antigen, or an amount that extends the survival of the individual, or that alleviates disease symptoms associated with expression of the antigen in the individual.

The method of the invention can be performed in conjunction with conventional therapies that are intended to treat a disease or disorder associated with the antigen. For example, if the method is used to enhance an immune response to a tumor antigen in an individual, treatment modalities including but not limited to chemotherapies, surgical interventions, and radiation therapy can be performed prior to, concurrently, or subsequent to the method of the invention.

As will be evidenced by the Examples presented herein, to develop a means of limiting the ability of cancer vaccines to interact with Treg cells in tumor-bearing mice, we first compared the generation of functional tumor-specific cellular responses by the 47-LDA peptide mimic presented to DCs either as a linear polypeptide in conjunction with universal Th epitopes or as a fusion protein with the murine IgG2a Fc fragment. We showed that the 47-LDA-Fcγ2a fusion protein-DC vaccine not only expanded tumor-specific $CD8^+$ T cells, but also induced primary immune responses after ACT of naïve splenocytes to tumor-bearing mice that underwent myeloablative TBI and BM transplantation. The 47-LDA-Fcγ2a vaccine-induced $CD8^+$ T cells inhibited growth of the primary tumors as well as protected the tumor-bearing mice from the development of minimal residual disease. On the other hand, protection elicited by the 47-LDA polypeptide-DC vaccine resulted in a delay of tumor growth, which was significant only after ACT in the myeloablative setting. The results of these studies are consistent with the findings that FcγRs are capable of modulating T cell-mediated immune responses during therapeutic vaccination in tumor-bearing mice.

The mechanisms responsible for the increased ability of 47-LDA-Fcγ2a$^+$ DCs to induce higher levels of tumor-specific immune responses compared to those generated by the 47-LDA$^+$ DCs remain to be elucidated. It is possible that the elevated number of IL-12-expressing cells within the 47-LDA-Fcγ2a$^+$ DC population compared to the 47-LDA$^+$ counterpart after LPS-induced maturation contributed to this effect since antigen-presenting cells that express IL-12 have augmented capacity to prime type 1 rather than Treg cell responses. This observation is further supported by the reduced expression of CCL22 chemokine in 47-LDA-Fcγ2a$^+$ DCs and lower proportion of Treg cells in 47-LDA-Fcγ2a'DC-immunized mice compared to animals that received the 47-LDA-DC vaccine. Our results are consistent with the previous findings that the character of the inflammatory environment can affect the balance between Teff and Treg cell activation by instructing the maturing DCs to adopt a stable propensity to interact with each of these T-cell types. It is noteworthy however that although alteration of DC functions has been suggested in the design of a cancer vaccine, tuning of DC responses to counteract the immunosuppression associated with tumor progression during therapeutic vaccination with a mimotope of tumor-associated antigens has not been extensively evaluated. Thus, these findings highlight a new application of peptide mimotopes for immunotherapy of cancer.

It is well established that activating and inhibitory low-affinity FcγRs are critical for the modulation of effector immune responses Their role in the induction of adaptive immunity showed that alteration in the function of activating/inhibitory receptors during administration of antigens to DCs in a form of immune complexes can influence activation of DCs in vivo and enhance antitumor T-cell responses. This notion is supported by the observation that selective blockade of inhibitory FcγRIIb receptor enables human DC maturation and immunity to antibody-coated tumor cells, and DCs from FcγRIIb-deficient mice show higher expression of co-stimulatory molecules which could account for an increased capacity to prime antigen-specific T cells. However, the use of large protein carriers creates difficulties in terms of reproducibility of the antigen binding that may endanger vaccine effectiveness and/or practical feasibility. Therefore, synthetic constructs encompassing the antigenic and helper epitopes as well as the Fc portion of IgG antibody with increased binding affinity to activating FcγRs should offer distinct advantages over immune complexes in terms of manufacturing and characterization. This also suggests that the ability of 47-LDA-Fcγ2a fusion protein to empower DCs to efficiently prime and expand specific $CD8^+$ CTL responses in tumor-bearing mice might lead to improved efficacy of tumor immunotherapy.

The study of antitumor immune responses after DC vaccines or surgery has shown that Treg cells are a fundamental obstacle to the development of T-cell memory in hosts bearing poorly immunogenic tumors. Although surgery currently remains the leading cure for solid tumors, memory T-cell responses may be required for the durable prevention of tumor recurrence and metastasis following surgery. As seen in most patients with cancer, our results showed that surgery or DC vaccine alone does not induce protection against poorly immunogenic tumor-associated antigens. However, in our model, surgery in combination with lymphodepletion, ACT and DC vaccination enables the development of long-lived tumor protection. Although we cannot exclude the possibility that the tumor itself served as the source of antigen, presumably priming T-cell responses against multitude of tumor antigens during induction of postsurgical immunity in the absence of Tregs, the antitumor immunity generated in the absence of the 47-LDA mimotope DC vaccination only extended the survival of tumor-bearing mice. In contrast, active immunization with 47-LDA-Fcγ2a fusion protein targeted to the activating FcγRs in a myeloablated tumor-bearing host led to a significant suppression of primary tumor and protection from the development of spontaneous metastatic disease.

While the use of ex vivo generated DCs provides a unique opportunity to avoid tumor-induced DC dysfunction and allows for precise manipulation of DC properties, the need for specialized cell culture facilities for the ex vivo manipulation of patient's cells prompted attempts to develop cell-free vaccines capable of targeting endogenous DCs within the bodies of tumor-bearing hosts. Such vaccines engineered to deliver tumor antigens or their mimotopes selectively to DCs can be coupled with strategies to induce DC polarization in vivo without any ex vivo treatment. Our results using the virotherapy approach with rOVV-47-LDA-Fcγ2a vector, which delivers the transgene directly to tumor lesions (data not shown) for secretion and crosspresentation by DCs, demonstrated the induction of protective Teff as well as memory T cells in the absence of any exogenous cytokine treatment, ACT, TBI, or ex vivo manipulation. Further investigation is required to better define the effect of crosspresentation of the virally-delivered 47-LDA-Fcγ2a fusion protein in the tumor microenvironment on the balance between Teffs and Tregs as well as the effectiveness and longevity of the virotherapy-induced antitumor immune responses. In this regard, several lines of evidence indicate that VV elicits innate immune responses through the TLR2/MyD88-dependent pathway, resulting in the production of proinflammatory cytokines, and a TLR-independent pathway, leading to the activation of IFN-β in vitro and in vivo. Because sustained stimulation of TLRs of the innate immunity is required for breaking established Treg-mediated tolerance in vivo and VV can provide TLR signals, this unique potency of VV as a vaccine vehicle can lead to activation of host defense and protect the mice from tumor challenge. Thus, the possibility of breaking $CD8^+$ T cell tolerance by the virus-based vaccines in the presence of $CD4^+CD25^+$ Tregs suggests that rOVV expressing the 47-LDA-Fcγ2a fusion protein or other tumor-associated antigens may prove an appealing alternative to DC vaccines for overcoming $CD4^+CD25^+$ T cell-mediated CD8 tolerance in vivo. In summary, this work stresses the importance of exploring the uptake and processing of tumor/self-antigens by DCs to activate immune effector cells and limit the ability of attracting anti-inflammatory Treg cells. Our findings illuminate a new paradigm for cancer immunotherapies aimed at the selective activation of the inflammatory versus regulatory type of immune cells.

The following Examples are intended to illustrate but not limit the invention.

EXAMPLE 1

This Example provides a description of the materials and methods used to obtain data presented herein.

Animals and Cell Lines

Female A/J mice, 6-8 weeks of age, were obtained from the Jackson Laboratory (Bar Harbor, Me.). The experimental procedures were performed in compliance with protocols approved by the Institutional Animal Care and Use Committee of the Roswell Park Cancer Institute. The murine NXS2 neuroblastoma cell line (provided by Dr. R. A. Reisfeld, The Scripps Res. Inst. La Jolla, Calif.) is a hybrid between the GD2-negative C1300 murine neuroblastoma (A/J background) and GD2-positive murine dorsal root ganglioma cells. The hybrid cell line was shown to be MHC class I syngeneic to A/J mice by its $H-2K^k$-positive/$H-2K^b$-negative phenotype (Lode, H. N., R. Xiang, T. Dreier, N. M. Varki, S. D. Gillies, and R. A. Reisfeld. 1998. Natural killer cell-mediated eradication of neuroblastoma metastases to bone marrow by targeted interleukin-2 therapy. Blood 91: 1706-1715.). The 14G2a hybridoma cell line secreting GD2-specific mAb (Mujoo, K., T. J. Kipps, H. M. Yang, D. A. Cheresh, U. Wargalla, D. J. Sander, and R. A. Reisfeld. 1989. Functional properties and effect on growth suppression of human neuroblastoma tumors by isotype switch variants of monoclonal antiganglioside GD2 antibody 14.18. Cancer Res 49: 2857-2861) was provided by Dr. R. A. Reisfeld (The Scripps Res. Inst.).

Generation of 47-LDA-Fcγ2a Fusion Protein

The construction of 47-LDA expression vector comprising tissue plasminogen activator secretory (tPA) signal sequence, two universal Th peptides PADRE [AKFVAAWTLKAAA SEQ ID NO:3; (Alexander, J., M. F. del Guercio, A. Maewal, L. Qiao, J. Fikes, R. W. Chesnut, J. Paulson, D. R. Bundle, S. DeFrees, and A. Sette. 2000. Linear PADRE T helper epitope and carbohydrate B cell epitope conjugates induce specific high titer IgG antibody responses. J Immunol 164: 1625-1633) and V3 loop of the HIV gp120 glycoprotein [CKRKIHIGPGQAFYT SEQ ID NO:4; (Ahluwalia, A., K. Gokulan, I. Nath, and D. N. Rao. 1997. Modification of delivery system enhances MHC nonrestricted immunogenicity of V3 loop region of HIV-1 gp120. Microbiol Immunol 41: 779-784) together with the 47-LDA mimetic peptide was reported elsewhere (Bolesta, E., A. Kowalczyk, A. Wierzbicki, P. Rotkiewicz, B. Bambach, C. Y. Tsao, I. Horwacik, A. Kolinski, H. Rokita, M. Brecher, X. Wang, S. Ferrone, and D. Kozbor. 2005. DNA vaccine expressing the mimotope of GD2 ganglioside induces protective GD2 cross-reactive antibody responses. Cancer Res 65: 3410-3418.). The murine 47-LDA-Fcγ2a fusion protein was generated by inserting the 47-LDA polypeptide coding sequence between the hEF1-HTLV promoter and the mouse IgG2a Fc region of the pFUSE-mIgG2Aa-Fc1 vector (InvivoGen, San Diego, Calif.) using the EcoRI and BglII restriction enzyme cleavage sites. Stable transfection of 293T cells was done with the 47-LDA-Fcγ2a fusion protein construct or sham vector using Lipofectamine Reagent (Invitrogen, Carlsbad, Calif.) followed by selection in zeocin-containing medium. The 47-LDA-Fcγ2a fusion protein was purified from culture supernatants of the transfected cells on Protein G column (GE Healthcare, Bio-Sciences Corp, Piscataway, N.J.). The fusion protein was analyzed by SDS-15% PAGE and immunoblotting with 14G2a mAb followed by ECL plus Western blotting detection system (Amersham Pharmacia Biotech) according to the protocol of the manufacturer.

Immunization

DCs were generated in vitro from BM precursors as previously described (Brinker, K. G., H. Garner, and J. R. Wright. 2003. Surfactant protein A modulates the differentiation of murine bone marrow-derived dendritic cells. Am J Physiol Lung Cell Mol Physiol 284: L232-241). Briefly, BM cells were harvested from the tibias and femurs of 6- to 8-week-old female A/J mice (n=5) and then cultured in complete medium supplemented with 10 ng/ml GM-CSF at 37° C. for 6 days. The medium was replenished every 2-3 days. On day 7, most of the nonadherent cells had acquired DC morphology and were CD11c high and CD80, CD86, CD40, and MHC class II low, as determined by flow cytometric analyses. DCs were pulsed for 5 h with 10 μg/ml of 47-LDA-Fcγ2a fusion protein or 47-LDA polypeptide (New England Peptide, LLC, Gardner, Mass.), incubated with LPS (1.0 μg/ml) for 1 h to induce maturation, washed and injected i.v. ($2\times10^6$) to mice (FIG. 1A). 20 μg of DNA plasmid-encoded IL-15 and IL-21 cytokines were injected i.m. at the time of vaccination and five days later, respectively.

Flow Cytometry

Immature DCs were incubated with biotin-labeled 47-LDA-Fcγ2a fusion protein or 47-LDA polypeptide followed by streptavidin-conjugated PE. For some experiments, DCs were stained with the following mAbs: anti-CD11c-FITC, anti-CD80-PE, anti-CD86-PE, anti-CD40-PE, or anti-MHC class II-PE (BD Bioscience, San Jose, Calif.). Splenocytes were labeled with anti-CD4-PE, anti-CD8-PE, anti-CD25-FITC (BD Bioscience) or the relevant isotype controls. Prior to specific antibody staining, cells were incubated with Fc blocker (anti-CD16/CD32 mAb) for 10 min. The cells were washed twice in HBSS containing 0.01% sodium azide and 1% FCS, fixed with 1% paraformaldehyde, and stored at 4° C. in the dark before analyses. Background staining was assessed using isotype controls which included the appropriate fluorochrome-conjugated or unconjugated mouse IgG1, IgG2a or IgG2b (BD Bioscience). The numbers of Treg cells in the axillary, brachial lymph nodes and spleen were determined by intracellular staining of $CD4^+CD25^+$ lymphocytes with anti-FoxP3-AlexaFluor 647 mAb (eBioscience, San Diego, Calif.) according to the manufacturer's protocol. The number of $CD4^+$ and $CD8^+$ splenocytes secreting IFN-γ or TNF-α was determined using anti-CD4-FITC and anti-CD8-FITC mAbs in conjunction with anti-IFN-γ-PE or anti-TNF-α-PE mAb (BD Bioscience). The intracellular expression of IL-12p70 in LPS-stimulated DCs was measured by staining with rat anti-mouse IL-12p70 mAb that detects an epitope within the IL-12p35 subunit and does not cross-react with IL-12p40 (R&D Systems, Inc.). The intracellular expression of CCL22 in LPS-stimulated DCs was determined by staining with rat anti-mouse CCL22 mAb (R&D Systems, Inc.). Sorting of 47-LDA-Fcγ2a$^+$, 47-LDA polytope$^+$ or $CD86^+$ DCs was performed on BD FACSAria™ Flow Cytometer (BD, Franklin Lakes, N.J.). All flow cytometric evaluations were performed on FACScan or FACSCalibur flow cytometer. After gating on forward and side scatter parameters, at least 10,000-gated events were routinely acquired and analyzed using CellQuest software (BD Bioscience).

Adoptive Transfer of T Cells and DC Vaccine

A/J mice (n=8-10 per group) were injected s.c. with $2\times10^6$ NXS2 neuroblastoma cells and treated 15 days later by i.v. injection with $CD8^+$-enriched splenocytes isolated from 47-LDA-Fcγ2a- or 47-LDA polytope-DC-immunized mice, as depicted in FIG. 1A. The $CD8^+$ splenocytes were negatively selected using paramagnetic Microbeads conjugated to anti-mouse CD4 (L3T4) and anti-mouse CD45R (B220) mAbs (MACS; Miltenyi Biotec) according to the manufacturer's instructions. The isolated $CD8^+$ splenocytes ($2\times10^7$) were incubated with LPS-matured 47-LDA polypeptide- or 47-LDA-Fc fusion protein-coated DCs. The mixtures of T cells and DCs (20:1 ratio) were injected i.v. to the lymphodepleted NXS2 tumor-bearing mice in the presence of rmIL-2 (1 µg/dose) as described (Zeng, R., R. Spolski, S. E. Finkelstein, S. Oh, P. E. Kovanen, C. S. Hinrichs, C. A. Pise-Masison, M. F. Radonovich, J. N. Brady, N. P. Restifo, J. A. Berzofsky, and W. J. Leonard. 2005. Synergy of IL-21 and IL-15 in regulating CD8+ T cell expansion and function. *J Exp Med* 201: 139-148). Lymphopenia in the tumor-bearing mice was induced by 5 Gy nonmyeloablative TBI or 9 Gy myeloablative TBI plus BM transfer ($10^7$ cells) one day prior to the ACT and vaccination (FIG. 1B). Control mice bearing established s.c. NXS2 tumors were irradiated with 5 Gy or 9 Gy plus BM transplantation. Mice were immunized in a 2-week interval with the DC vaccine in the presence of IL-15 and IL-21 vectors as described (Kowalczyk, A., A. Wierzbicki, M. Gil, B. Bambach, Y. Kaneko, H. Rokita, E. Repasky, R. Fenstermaker, M. Brecher, M. Ciesielski, and D. Kozbor. 2007. Induction of protective immune responses against NXS2 neuroblastoma challenge in mice by immunotherapy with GD2 mimotope vaccine and IL-15 and IL-21 gene delivery. *Cancer Immunol Immunother* 56: 1443-1458). Tumor growth was monitored by measuring s.c. tumors once to thrice a week with a microcaliper and determining tumor volume (width×length×width/2=mm$^3$).

For the immunotherapy of disseminated disease, NXS2-bearing mice underwent nonmyeloablative (5 Gy) or myeloablative (9 Gy) TBI at the time of tumor resection (FIG. 1C). One day after tumor excision, the mice received ACT of splenocytes ($2\times10^7$) from the immunized or naïve mice together with the DC vaccine. Mice were immunized in a 2-week interval with the DC vaccine in the presence of IL-15 and IL-21 vectors as described (Kowalczyk, A., A. Wierzbicki, M. Gil, B. Bambach, Y. Kaneko, H. Rokita, E. Repasky, R. Fenstermaker, M. Brecher, M. Ciesielski, and D. Kozbor. 2007. Induction of protective immune responses against NXS2 neuroblastoma challenge in mice by immunotherapy with GD2 mimotope vaccine and IL-15 and IL-21 gene delivery. *Cancer Immunol Immunother* 56: 1443-1458). The control mice had the primary tumor excised with or without TBI and BM transplantation. Survival was defined as the point at which mice were sacrificed due to extensive tumor growth. Kaplan-Meier survival plots were prepared, and significance was determined using logrank Mantel-Cox method.

In Vitro Analyses of Vaccine-Induced IFN-γ and TNF-α Expression and T Cell Proliferation Splenocytes from A/J mice immunized with the 47-LDA-Fcγ2a- or 47-LDA polypeptide-coated DCs were analyzed for IFN-γ and TNF-α expression after overnight stimulation with 47-LDA-expressing DCs at the 20:1 ratio. Cells isolated from sham vector-immunized mice served as controls. To investigate the induction of Treg cells in mice immunized with 47-LDA-DC and 47-LDA-Fcγ2a-DC vaccines, the spleen, axillary and brachial lymph nodes were removed from the immunized mice three weeks after the last immunization and analyzed for numbers of Treg cells by staining with anti-CD4-PE, anti-CD25-FITC, and anti-FoxP3-Alexa Fluor 647 mAbs, or the relevant isotype controls. To analyze the effect of Treg cells on Teff cell proliferation, $CD8^+$ T cells from the 47-LDA-DC or 47-LDA-Fcγ2a-DC vaccine immunized mice were loaded with 25 µM carboxyfluorescein succinimidyl ester (CFSE; Molecular Probes, Eugene, Oreg.) for 10 min at 37° C. and cultured with 47-LDA-expressing syngeneic DCs (ratio 20:1) for 72 h in the presence or absence of Treg cells (ratio 1:1). Cells were stained with PE-conjugated anti-CD8 mAbs and analyzed by flow cytometry. The Treg cell populations were isolated using $CD4^+CD25^+$ regulatory T cell isolation kit (Miltenyi) according to the manufacturer's protocol.

To analyze proliferative $CD4^+$ and $CD8^+$ T cell responses in tumor-bearing and tumor-free mice after ACT and DC vaccination, splenocytes were labeled with 25 µM CFSE and incubated with 47-LDA-expressing DCs for 72 h. Cells were stained with PE-conjugated anti-CD4 or anti-CD8 mAbs and analyzed by flow cytometry.

CTL Assay

Splenocytes were cultured with 47-LDA-expressing DCs at the 20:1 ratio in 15% T cell stimulatory factor (T-STIM™ Culture Supplement, Collaborative Biomedical Products, Bedford, Mass.) as a source of exogenous IL-2. After three days of stimulation, cells were split and cultured in medium supplemented with murine rIL-2 (0.3 ng/ml) (BD Bioscience). Prior to stimulation, $CD8^+$ T cells were isolated by negative selection using T cell enrichment columns (Miltenyi) according to the manufacturer's protocol. The cytolytic activity of CTLs against NXS2 tumor cells was analyzed 5 days later by a standard 4-h $^{51}$Cr-release assay. The percent of specific lysis was calculated as: ([cpm experimental release–cpm spontaneous release]/[cpm maximum release–cpm spontaneous release])×100. Maximum release was determined from supernatants of cells that were lysed by addition of 5% Triton X-100. Spontaneous release was determined from target cells incubated with medium only.

Generation of rOVVs Expressing Enhanced Green Fluorescence Protein (EGFP) and the 47-LDA-Fcγ2a Fusion Protein for Oncolytic Virotherapy-Based Cancer Vaccine There are a variety of ways by which rOVVs suitable for use in the present invention can be made. In a particular demonstration the rOVVs expressing EGFP and 47-LDA-Fcγ2a fusion protein were generated by homologous recombination in CV-1 cells using VSC20 vaccinia virus and the vaccinia shuttle plasmids pSEL-EGFP and pCB023-47-LDA-Fcγ2a, respectively. The parental vaccinia virus was VSC20 with lacZ gene cloned in place of the VGF gene. The VSC20 vaccinia virus is described in U.S. patent publication no. 20070154458, from which the description of the VSC20 virus is incorporated herein by reference.

The pCB023-47-LDA-Fcγ2a shuttle plasmid was generated by cloning the 47-LDA-Fcγ2a fusion protein gene into the EcoRI and SmaI restriction enzyme sites of pCB023. After the DNA sequence verification, the secretion of the 47-LDA-Fcγ2a fusion protein into culture supernatant of 293T cell transfectants was confirmed by immunoblotting with 14G2a mAb. Multiple plaques of the recombinant viruses were isolated in TK− cells by BrdU selection. After amplification on HeLa cells, the rOVV-EGFP and rOVV-47-LDA-Fcγ2a viruses were purified over the sucrose gradient, titered and used for in vitro and in vivo studies in NXS2 cells. The expression of EGFP in rOVV-EGFP-infected NXS2 cells was confirmed by immunofluorescence microscopy, whereas secretion of the 47-LDA-Fcγ2a fusion protein from rOVV-47-LDA-Fcγ2a-infected NXS2 cells was determined by immunoblotting with 14G2a mAb.

For the oncolytic virotherapy-based vaccine, A/J mice (n=10) were injected s.c. with $2 \times 10^6$ NXS2 cells and treated 15 days later with i.v. injection of $10^8$ plaque forming units (PFUs) of the rOVV-47-LDA-Fcγ2a or rOVV-EGFP vector. Tumor-bearing mice that were treated with PBS served as controls. Survival was defined as the point at which mice were sacrificed due to extensive tumor growth. Kaplan-Meier survival plots were prepared, and significance was determined using logrank Mantel-Cox method.

Statistical Analyses

The statistical significance of the difference between groups was performed using a two-tailed Student's t test assuming equal variance. The P values for the pairwise group comparisons for the average tumor growth were computed using the nonparametric Wilcoxon's rank-sum test. Kaplan-Meier survival plots were prepared and median survival times were determined for NXS2-challenged groups of mice. Statistical differences in the survival across groups were assessed using the logrank Mantel-Cox method. Data were presented as arithmetic mean±SD and analyzed using the JMP program (SAS Institute Inc., Cary, N.C.) on a Windows-based platform.

EXAMPLE 2

Characterization of Murine 47-LDA-Fcγ2a Fusion Protein

The murine 47-LDA-Fcγ2a fusion protein was generated by inserting the relevant coding sequence [including the tissue plasminogen activator secretory (tPA) signal sequence, two universal Th peptides, and the 47-LDA mimotope] in-frame between the hEF1-HTLV promoter and the mouse IgG2a Fc region of the pFUSE-mIgG2Aa-Fc1 vector using the EcoRI and BglII restriction enzyme cleavage sites. After sequencing of the 47-LDA-Fcγ2a construct to confirm the presence of an uncorrupted open reading frame, immunofluorescence staining of 47-LDA-Fcγ2-transfected 293T cells with 14G2a mAb followed by a flow cytometry analysis was done 48 h after transfection to determine the expression of the fusion protein (not shown). The secretion of the fusion protein from 47-LDA-Fcγ2a stable transfectants, selected in zeocin-containing medium, was confirmed by immunoblotting of the culture supernatant with 14G2a mAb. As shown in FIG. 2A, a prominent band of 31.9 kDa was detected with 14G2a mAb in the culture supernatant harvested from 47-LDA-Fcγ2a transfectants. No band was present in the supernatant prepared from cell transfected with the sham plasmid. The 47-LDA polypeptide of molecular mass of 6.6 kDa, which was included in the analysis as a positive control, was clearly recognized by 14G2a mAb. Altogether, these results showed that the GD2 mimotope expressed in the context of 47-LDA-Fcγ2a fusion protein retained its native antigenic determinants of the synthetic peptide recognized by 14G2a mAb.

The binding of 47-LDA-Fcγ2a fusion protein and 47-LDA polypeptide to BM-derived immature DCs was determined by a flow cytometry analysis. As shown in FIG. 2B, over 50% of CD11c+ DCs reacted with biotinylated 47-LDA-Fcγ2a fusion protein or the biotin-labeled 47-LDA polypeptide. The binding of 47-LDA-Fcγ2a fusion protein, but not 47-LDA polypeptide, was inhibited by the Fc blocking antibody CD16/32 indicating a specific interaction between the 47-LDA-Fcγ2a fusion protein and its cellular ligands. It is noteworthy however that the binding of 47-LDA-Fcγ2a fusion protein to the FcγRs had no effect on DC maturation since addition of LPS was necessary to upregulate the surface expression of CD86, CD40, and CD86 antigens (not shown).

Because the activating and inhibitory FcγRs are critical for the modulation of effector immune responses during administration of antigens to DCs in the form of immune complexes and IL-12 is a key cytokine involved in the generation of type-1 immunity, we investigated whether DCs that interact with 47-LDA polypeptide or 47-LDA-Fcγ2a fusion protein differ in their ability to express IL-12p70 upon stimulation with LPS. For these experiments, 47-LDA+ and 47-LDA-Fcγ2a+ DCs as well as their negative counterparts were obtained by cell sorting. DCs positive or negative for CD86 expression were included as a specificity control (FIGS. 2B and C). The sorted DC populations were stimulated overnight with 1 μg/ml of LPS and analyzed for IL-12p70 expression by intracellular staining and a flow cytometric analysis. FIG. 2C shows that 47-LDA-Fcγ2a+ DCs expressed significantly higher levels of IL-12p70 than their negative counterparts after stimulation with LPS (P=0.008), whereas comparable levels of IL-12p70 were measured in 47-LDA+ and 47-LDA− DC populations or those sorted for the presence or absence of CD86 antigen expression. A parallel expression study of the Treg-attracting CCL22 chemokine in the sorted and LPS-stimulated 47-LDA+ and 47-LDA-Fcγ2a+ DCs revealed approximately twofold higher numbers of CCL22-positive cells in the former DC population (FIGS. 3A and B; P=0.037).

Enhanced Immunostimulatory Activity of 47-LDA-Fcγ2a-Pulsed DCs In Vivo

Figure 3:
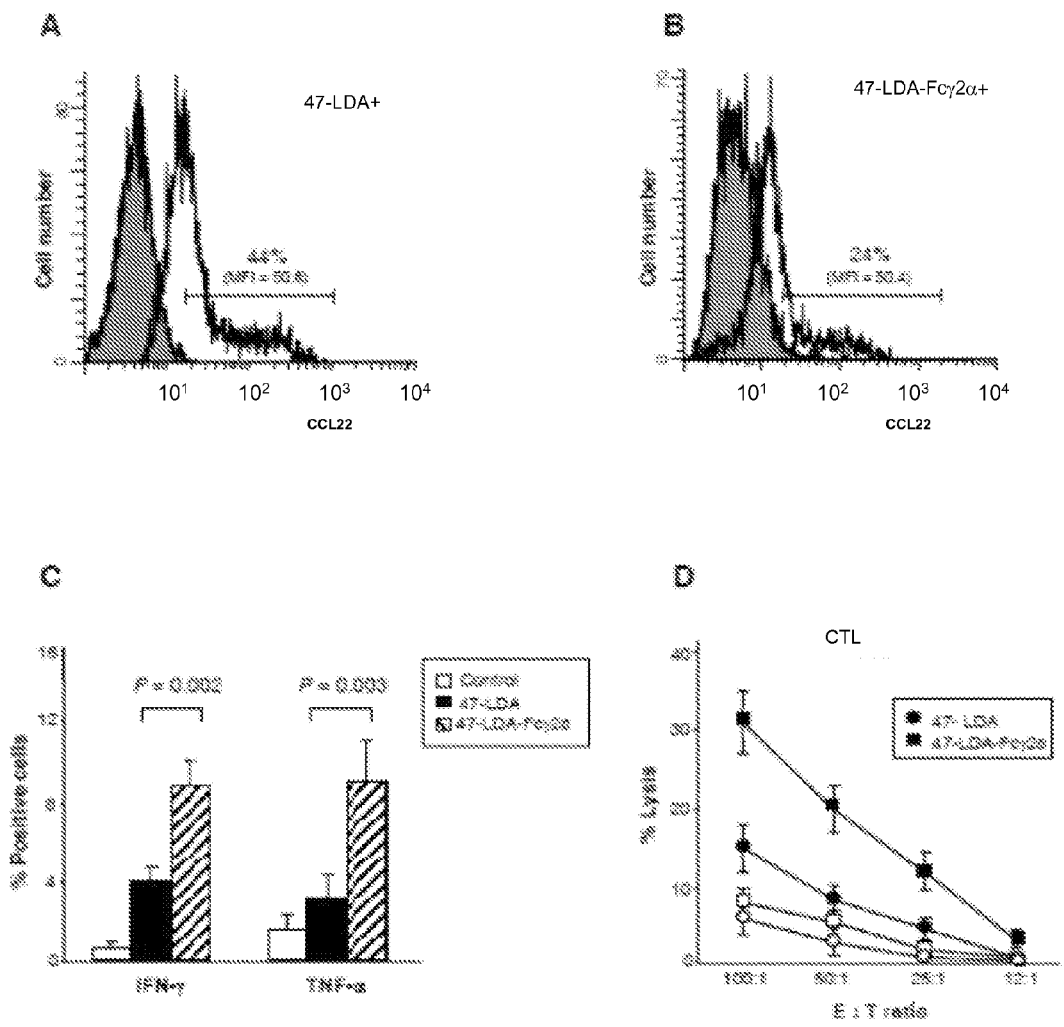
FIG. 3. Differential expression of CCL22 in 47-LDA$^+$ and 47-LDA-Fcγ2a$^+$ DCs after LPS stimulation and induction of IFN-γ and TNF-α in CD4 splenocytes by 47-LDA- and 47-LDA-Fcγ2a-DC vaccines. Immature DCs were stained with biotinylated 47-LDA polypeptide or 47-LDA-Fcγ2a fusion protein followed by streptavidin-PE. The 47-LDA$^+$ (A) and 47-LDA-Fcγ2a$^+$ (B) DCs were sorted on BD FACSAria™ flow cytometer, incubated with 1 μg/mlLPS for 24 h and analyzed for CCL22 expression by intracellular staining with rat anti-mouse CCL22 mAb, followed by goat anti-rat secondary antibody. The MFI and percent of cells positive for CCL22 expression are indicated. Light gray area denotes background staining assessed using an isotype control Ab. Data are from one representative experiment of three performed. C, Expression of IFN-γ and TNF-α in splenocytes of mice immunized with 47-LDA-DC and 47-LDA-Fcγ2a-DC vaccines (black and hatched bars, respectively). A/J mice (n=5) were immunized three times with DCs coated with 47-LDA polypeptide or 47-LDA-Fcγ2a fusion protein after LPS-induced maturation in the presence of IL-15 and IL-21 vectors. Cells isolated from mice immunized with LPS-treated DC served as controls (open bars). Three weeks after the last immunization, the expression of IFN-γ and TNF-α in CD4 splenocytes was analyzed by intracellular staining after overnight stimulation with DCs expressing the 47-LDA mimotope. D, NXS2 neuroblastoma-specific CTL responses. $CD8^+$ splenocytes from mice immunized with 47-LDA-DC (●) and 47-LDA-Fcγ2a-DC (■) vaccines were obtained by negative selection. Cells were cultured with 47-LDA-expressing DCs (black symbols) or sham plasmid-transfected DCs (open symbols) at the 20:1 ratio as described in the Materials and Methods section. The CTL activities against NXS2 cells were analyzed in a standard $^{51}$Cr-release assay. All determinations were made in triplicate samples, and the SD was <10%. Results are presented as the means±SD of four independent experiments.

The differences in the expression levels of IL-12 and CCL22 between LPS-stimulated 47-LDA-Fcγ2a+ DC and 47-LDA+ DCs suggest that these cells may have different ability to interact with Teff and Treg cells in vivo. Therefore, we investigated the induction of tumor-specific Th1 and CTL responses after immunization of A/J mice with 47-LDA-Fcγ2a- and 47-LDA-DC vaccines (FIG. 1A). Each DC vaccine was delivered by i.v. injection three times in a 2-week interval together with DNA plasmid-encoded IL-15 and IL-21 delivered i.m. at the time of vaccination and five days later, respectively (Kowalczyk, A., A. Wierzbicki, M. Gil, B. Bambach, Y. Kaneko, H. Rokita, E. Repasky, R. Fenstermaker, M. Brecher, M. Ciesielski, and D. Kozbor. 2007. Induction of protective immune responses against NXS2 neuroblastoma challenge in mice by immunotherapy with GD2 mimotope vaccine and IL-15 and IL-21 gene delivery. *Cancer Immunol Immunother* 56: 1443-1458). Three weeks after the last immunization, CD4+ splenocytes from the immunized mice were analyzed for IFN-γ and TNF-α production by intracellular staining and flow cytometry after overnight stimulation with 47-LDA-expressing DCs. Cells isolated from mice immunized with DCs and IL-15 and IL-21 vectors were included as controls. As shown in FIG. 3C, the numbers of IFN-γ- and TNF-α-producing CD4+ cells were over four-fold higher in mice immunized with the 47-LDA-Fcγ2a fusion protein-coated DCs than in control animals, and over twofold higher than responses induced by the 47-LDA-DC vaccine (P=0.002 and P=0.003, respectively). The increases in IFN-γ-producing CD4+ T cell responses after 47-LDA-Fcγ2a fusion protein vaccine were associated with higher CD8+ T cell-mediated cytotoxic activities against NXS2 neuroblastoma tumor compared with those induced by the 47-LDA polytope-coated DCs over a broad range of E:T ratio (FIG. 3D).

Figure 4:
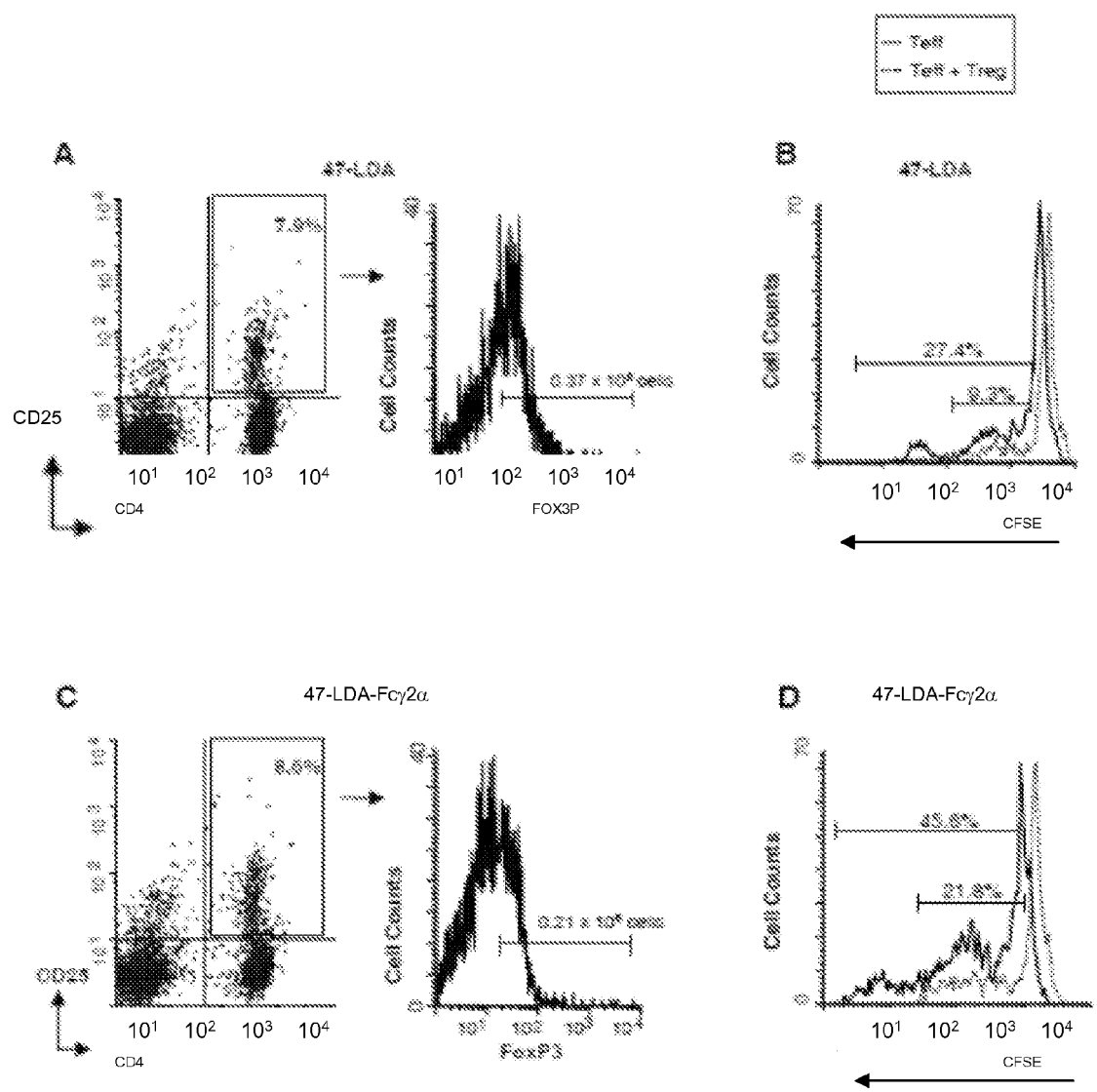
FIG. 4. Analyses of Treg cell induction and function in mice immunized with 47-LDA-DC and 47-LDA-Fcγ2a-DC vaccines. Three weeks after the last immunization with 47-LDA-DCs (A) or 47-LDA-Fcγ2a-DCs (C), the axillary lymph nodes were removed and analyzed for Treg cell expression by staining with anti-CD4-PE, anti-CD25-FITC and anti-FoxP3-AlexaFluor 647 mAbs, or the relevant isotype controls. The histograms illustrate the FoxP3 expression in the gated populations ($CD4^+CD25^+$ cells). To analyze the effect of Treg cells on Teff cell proliferation, $CD8^+$ cells from 47-LDA-DC (B) or 47-LDA-Fcγ2a-DC (D) vaccine immunized mice were loaded with CFSE and cultured with 47-LDA-expressing syngeneic DCs (ratio 20:1) for 72 h in the presence or absence of Treg cells (ratio 1:1). Cells were stained with PE-conjugated anti-CD8 mAbs and analyzed by flow cytometry. The percentage of cells that underwent more than one round of cell division is indicated. Data are from one representative experiment of three performed.

We also examined the induction of Treg cells after 47-LDA and 47-LDA-Fcγ2a-DC vaccines by a flow cytometric analysis of CD4+CD25+FoxP3+ lymphocytes in the axillary, brachial lymph nodes and spleen. In the axillary lymph nodes of 47-LDA-immunized mice, the absolute numbers of FoxP3+ cells within the CD4+CD25+ population ranged from $0.31\times10^6$ to $0.42\times10^6$ cells (FIG. 4A), and were ~2-fold higher compared to the animals immunized with the 47-LDA-Fcγ2a-DC vaccine ($0.36\pm0.06$ vs. $0.19\pm0.04$; P=0.03). In the latter group of mice, the numbers of CD4+CD25+ lymphocytes positive for intracellular FoxP3 expression ranged from $0.17\times10^6$ to $0.24\times10^6$ cells (FIG. 4C). Similar differences in frequencies of Treg cells were detected in the brachial lymph nodes and spleen of the immunized mice (data not shown). When CFSE-labeled CD8+ lymphocytes and Treg cells prepared from 47-LDA-DC- and 47-LDA-Fcγ2a-DC-immunized mice were mixed at a 1:1 ratio and cocultured with the respective LPS-matured 47-LDA+ DCs and 47-LDA-Fcγ2a+ DCs, both populations of Treg cells suppressed the expansion of Teff cells (FIGS. 4B and D, respectively). However, the proliferation rate of Teff cells in 47-LDA-Fcγ2a+ DC-stimulated cultures were significantly higher compared to stimulation elicited with 47-LDA+ DCs (P=0.02).

Myeloablative TBI in Combination with the 47-LDA-Fcγ2a-DC Vaccine Enhances ACT Therapy To compare the therapeutic efficacy of the 47-LDA- and 47-LDA-Fcγ2a-DC vaccines, we performed ACT experiments with antigen-experienced CD8+ splenocytes in NXS2 tumor-bearing A/J mice (FIG. 1B). The CD8+ T cells were injected i.v. to the NXS2-bearing mice together with 47-LDA- or 47-LDA-Fcγ2a-DC vaccine to induce proliferation of Teff cells and mount a secondary response upon adoptive transfer to the lymphodepleted host. FIG. 5A shows that lymphodepletion with a nonmyeloablative (5 Gy) regimen prior to ACT and 47-LDA polypeptide-coated DC vaccine had a background effect on inhibition of tumor growth (P=0.28). The antitumor efficacy of the adoptively transferred CD8+ T cells was augmented after myeloablative (9 Gy) TBI, as determined by extension of the overall survival time of the treated mice from 25 to 70 days (FIG. 5A; P=0.007). We found that the myeloablative regimen was particularly effective in combination with adoptively transferred CD8+ splenocytes delivered together with 47-LDA-Fcγ2a-DCs. As shown in FIG. 5B, the latter treatment resulted in complete remission of tumor growth in 22% of NXS2-bearing animals that received myeloablative dose of TBI accompanied by a transplantation of syngeneic BM from naïve mice (P=0.0003). It is noteworthy that although the therapy with CD8+ T cells stimulated with 47-LDA-Fcγ2a-DC vaccine in the nonmyeloablative setting did not show complete tumor resolution, there was a significant prolongation of survival in the treated mice compared to the control group (FIG. 5B; P=0.015). The antitumor efficacy of the ACT was specific since all control mice developed progressively growing tumors and had to be sacrificed by day 25.

Control of Metastatic Disease by Adoptively Transferred CD8+ Splenocytes and 47-LDA-Fcγ2a-DC Vaccine The ability of NXS2 neuroblastoma to develop spontaneous metastases after excision of the primary tumor, provided a model for investigating the efficacy of adoptively transferred CD8+ splenocytes to control disseminated disease (FIG. 1C). In view of the accumulating evidence that curative surgery in conjunction with depletion of Treg cells enables the development of long-lived tumor protection and CD8+ T cell memory (9), NXS2 tumor-bearing mice underwent nonmyeloablative (5 Gy) or myeloablative (9 Gy) TBI at the time of tumor excision and ACT of antigen-experienced CD8+ splenocytes. As shown in FIG. 5C, transfer of CD8+ T cells expanded by 47-LDA polypeptide-coated DCs delayed progression of the metastatic disease that was observed only in the myeloablated mice (P=0.024). Tumor-free survival was not observed in this group of animals.

The antitumor efficacy of the adoptively transferred CD8+ T cells was significantly enhanced by the ACT and 47-LDA-Fcγ2a-DC vaccination as only two of six NXS2-challenged mice that received 5 Gy TBI prior to the ACT and 47-LDA-Fcγ2a-DC vaccine developed spontaneous metastases within a 50-day period of the treatment (FIG. 5D; P=0.003). The remaining mice in this group exhibited a delay in progression of the metastatic disease with the longest survival time of 90 days. As expected, the highest antitumor effectiveness of the adoptively-transferred splenocytes, with over 80% of tumor-free survival during a period of 120 days, was observed after a myeloablative regimen and ACT with 47-LDA-Fcγ2a-DC vaccine (FIG. 5D; P<0.001). On the other hand, the control mice that had the primary tumor excised and received TBI had to be sacrificed by day 40 due to disease progression. The metastatic lesions developed primarily in the brachial and axillary lymph nodes, and were less frequent in liver, spleen and BM as determined by staining with NXS2-reacting 14G2a mAb and RT-PCR analyses (data not shown).

Inhibition of Metastatic Disease by Primary Immune Responses Induced by the 47-LDA-Fcγ2a-DC Vaccine We next investigated the ability of 47-LDA- and 47-LDA-Fcγ2a-DC vaccines to induce antitumor immune responses capable of inhibiting metastatic disease after adoptive transfer of naïve splenocytes to myeloablated mice that had the primary tumor resected prior to the treatment initiation (FIG. 5E). For these experiments, total population of naïve splenocytes was used for ACT because CD4+ T cells are required for providing CD8+ T cells with growth factors and also eliciting antitumor responses. FIG. 5E shows that although the measurable therapeutic impact of the in vivo stimulated naïve T cells in NXS2-bearing mice was lower compared to that mediated by the antigen-experienced CD8+ T cells, 20% treated mice remained tumor-free 100 days after ACT with 47-LDA-Fcγ2a-DC vaccine (P=0.007). The 47-LDA+ DC vaccine was also capable of inducing antitumor T cells responses, albeit to a smaller degree. The control mice that had the primary tumor excised developed metastatic disease within the first 2 months of treatment, indicating a significant efficacy of the tumor-specific T cells induced by active immunization with 47-LDA-Fcγ2a-DC vaccine in NXS2-bearing mice.

Cellular Responses in Tumor-Bearing and Tumor-Free Mice after ACT and DC Vaccination We next investigated cellular responses in tumor-bearing and tumor-free mice after ACT and DC vaccines. Both therapeutic 47-LDA- and 47-LDA-Fcγ2a-DC vaccines were delivered to myeloablated mice after excision of the primary NXS2 tumor together with adoptively transferred naïve splenocytes and analyzed for induction of Teff cells. As no tumor-free survival was observed after ACT and immunization with 47-LDA$^+$ DC vaccine, animals with visible metastatic lesions in lymph nodes were examined for antitumor immune responses in the spleen. As shown in FIG. 6A, less than 15% of CD4$^+$ or CD8$^+$ splenocytes in the tumor-bearing mice underwent in vitro division after 72-h stimulation with 47-LDA-expressing DCs, and the CTL responses to NXS2 cells were at a background level (FIG. 6B). In contrast, a robust proliferation of CD4$^+$ and CD8$^+$ splenocytes (range 55% to 69% and 39% to 46%, respectively) was detected in tumor-free mice after receiving ACT and 47-LDA-Fcγ2a-DC vaccine (FIG. 6C). The proliferative responses were also associated with antitumor CTL activities against NXS2 cells (FIG. 6D).

Figure 7:
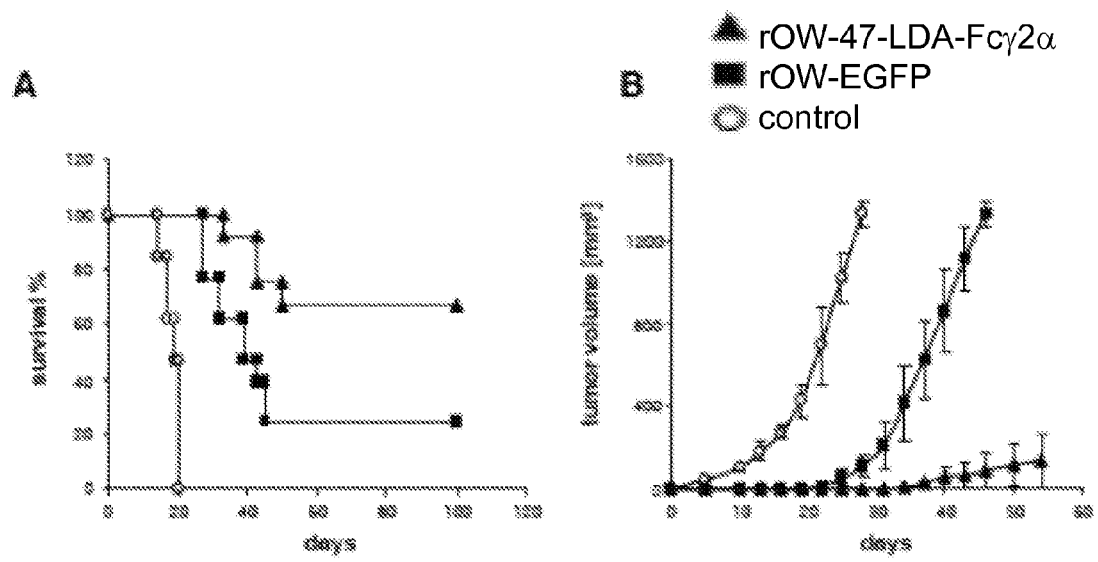
FIG. 7. Therapeutic oncolytic virotherapy-based cancer vaccine with rOVV-EGFP or rOVV-47-LDA-Fcγ2a fusion protein. A, Inhibition of tumor growth by rOVV-47-LDA-Fcγ2a vector. A/J mice (n=10) were injected s.c. with $2\times10^6$ NXS2 cells and treated 15 days later with i.v. injection of $10^8$ PFU of rOVV-47-LDA-Fcγ2a (▲) or rOVV-EGFP(■) vector. Tumor-bearing mice that were treated with PBS served as controls (○). Survival was defined as the point at which mice were sacrificed due to extensive tumor growth. Kaplan-Meier survival plots were prepared, and significance was determined using logrank Mantel-Cox method. B, Tumor-specific immune memory protected mice from NXS2 re-challenge. Tumor-free mice after treatment with rOVV-47-LDA-Fcγ2a (▲) or rOVV-EGFP (■) vector were re-challenged with NXS2 cells. Untreated mice challenged with NXS2 tumor served as controls (○). Animals were examined daily until the tumor became palpable, after which tumor growth was monitored by measuring s.c. tumors once to thrice a week.

Virotherapy-Based Cancer Vaccine with rOVV Expressing 47-LDA-Fcγ2a Fusion Protein To determine that the antitumor effect of 47-LDA-Fcγ2a-DC vaccine is not limited to the ACT in an irradiated tumor-bearing host, we next examined the therapeutic efficacy of the 47-LDA-Fcγ2a fusion protein expressed by the rOVV vaccinia virus. Because the oncolytic TK$^-$, VGF$^-$ mutant of vaccinia rOVV-47-LDA-Fcγ2a exhibits tumor-specific replication, it was anticipated that the fusion protein will be secreted from the infected cells and crosspresented by tumor-infiltrating DCs at the site of oncolysis. In parallel studies, an additional group of NXS2 tumor-bearing mice was injected with the rOVV-EGFP vector as a specificity control to determine the extent of protection elicited by tumor-associated antigens released from virally-infected NXS2 cells. Animals were examined for tumor growth by measuring s.c. tumors once to thrice a week. As shown in FIG. 7A, approximately 25% of NXS2-bearing mice that were treated with the control rOVV-EGFP vector became tumor-free. In contrast, all tumor-bearing mice that were treated with PBS instead of the viral vector developed progressively growing tumors and had to be sacrificed by day 20. The highest antitumor effectiveness, characterized by over 60% tumor-free survival for a period of 100 days, was observed in tumor-bearing mice after the oncolytic immunovirotherapy with rOVV-47-LDA-Fcγ2a vector (FIG. 7A; P=0.0004).

To obtain a more comprehensive understanding of the effect of oncolytic virotherapy treatment on the memory cell development in a tumor-bearing host, NXS2-challenged mice (n=6), which remained free of tumor for at least 40 days after rOVV-EGFP or rOVV-47-LDA-Fcγ2a treatment, were re-challenged s.c. with 10$^6$ NXS2 cells. FIG. 7B shows that all rOVV-EGFP-treated mice developed progressively growing tumor upon re-challenge with NXS2 tumor. There was however a 20-day delay in the initiation of tumor growth in the rOVV-EGFP-treated mice compared to the untreated animals. This finding is consistent with the ability of rOVV to induce antitumor immune responses due to uptake of apoptotic cells by DCs and crosspresentation of tumor antigens during oncolytic virotherapy (Li, Q. X., G. Liu, and F. Wong-Staal. 2008. Oncolytic virotherapy as a personalized cancer vaccine. *Int J Cancer* 123: 493-499.). On the other hand, only one of six rOVV-47-LDA-Fcγ2a-treated and NXS2 re-challenged mice developed slowly progressing tumor 35 days after tumor inoculation, reflecting a significant antitumor influence of the 47-LDA-Fcγ2a-induced immunity compared to rOVV-EGFP- or PBS-treated mice (FIG. 7B, P<0.001).

EXAMPLE 3

This Example provides a demonstration of one embodiment of the method used to inhibit the growth of two distinct tumors in a clinically relevant mouse model.

We expressed a novel anticancer agent CTCE-9908 that is the CXCR4 chemokine receptor antagonist. This peptide antagonist of CXCR4 (amino acid sequence: KGVSLSYR-K-RYSLSVGK; SEQ ID NO:5) is a dimer of the N-terminal region of SDF-1 (CXCL12) chemokine CTCE-9908 blocks the interaction of the CXCR4 receptor with CXCL12, which is critical in the infiltration of organ tissue by metastatic cells, thereby reducing tumor metastasis. CXCR4 receptors are expressed on many tumor cell types. The CTCE-9908 peptide has been developed by Chemokine Therapeutics, Vancouver, Canada and been used in Phase I/II clinical trials in late stage cancer patients.

We expressed a CTCE-9908 peptide (SEQ ID NO:6) in the context of the activating murine and human IgG2a and IgG1 Fc fragments, respectively, using DNA plasmids or oncolytic recombinant vaccinia viruses. The Fc receptor with naturally present disulfide bonds is used to preserve the dimeric structure of the CTCE-9908 peptide. Thus, the invention takes advantage of the naturally occurring disulfide bonds that form between Fc heavy chains to bring monomeric units which each consists of SEQ ID NO:6 in spatial proximity. This mimics the dimerization of the CTCE-9908 peptide (SEQ ID NO:5) without the need to provide two copies of the monomeric unit in the same peptide (wherein the C-terminal unit has the reverse orientation as compared to the N-terminal unit, as in SEQ ID NO:5). It also eliminates the requirement to have a linking amino acid, such as the K in the R-K-R sequence in the CTCE-9908 peptide. Further advantages include but are not necessarily limited to the presentation of the dimer in physical association (i.e., in the same polypeptide) with T helper epitopes as further described herein.

Figure 8:
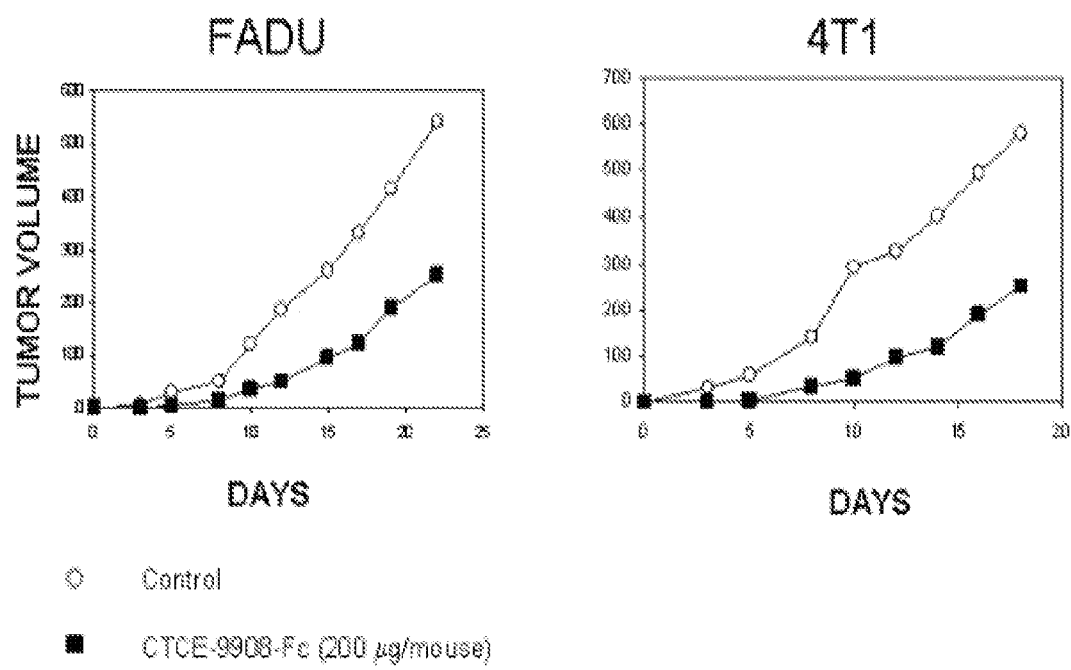
FIG. 8 provides a graphical representation of data showing that the invention is effective to inhibit growth of FADU and 4T1 tumors in a clinically relevant mouse model. To obtain the data summarized in FIG. 8, mice were implanted subcutaneously (s.c.) with FACU or 4T1 tumor cells. The CTCE-9908-Fc fusion protein (200 microgram/mouse), purified on protein G column from supernatant of transfected cells, was delivered daily by intravenous injection. Tumor growth was monitored by measuring s.c. tumors once to three times a week with a microcaliper and determining tumor volume (width×length/width/$2=mm^3$).

As can be seen from FIG. 8, our experiments performed in murine syngeneic (T41 breast carcinoma) and xenograft (FADU human head and neck carcinoma) models with the murine version of the CTCE-fusion protein (200 μg/mouse) showed antitumor efficacy of the CTCE-9908 peptide in the context of the activating Fc fusion protein.

EXAMPLE 4

To target CXCR4 on breast carcinoma and stromal cells (cancer-associated fibroblasts (CAFs), vascular endothelial cells and myeloid-derived suppressor cells (MDSCs)), we devised a strategy that led to inhibition of primary and metastatic growth of a highly aggressive triple-negative murine 4T1 tumor in syngeneic mice. The strategy that has led to tumor-free survival (meaning we did not detect any remaining tumor) is a combination of oncolytic virotherapy with OVV expressing the antagonist of CXCR4 followed by treatment with a tumor-vascular disrupting agent (tumor-VDA) (ASA404; (vadimezan)) that targets the blood vessels that nourish tumors. Thus, in one embodiment, the method of the invention includes administering to an individual a tumor-vascular disrupting agent. In one embodiment, the tumor vascular disrupting agent is the compound referred to in the art as ASA404 (vadimezan), which was described in Tozer, G. M., Kanthou, C. and Baguley, B. C., Disrupting tumour blood vessels. *Nat Rev Cancer* 2005. 5: 423-435. ASA404 is a commercially available compound. For example, Selleck (Houston, Tex. USA) offers ASA404 under the product name DMXAA, catalog number S1537.

The major mechanism of ASA404-induced vascular shutdown is believed to be increased vascular permeability that results in fluid extravasation, plasma loss and major pressure differences within the tumor that contribute to the eventual loss of blood flow. In this regard, we have used contrast enhanced-MRI to analyze of 4T1 vascular response to ASA404. A panel of images showed increased extravasation of the contrast agent s visible at 2 h post treatment (compared to pretreatment measurements. A further increase in contrast agent concentration was after 4 h due to alteration in vascular permeability. (Data not shown.)

Figure 9:
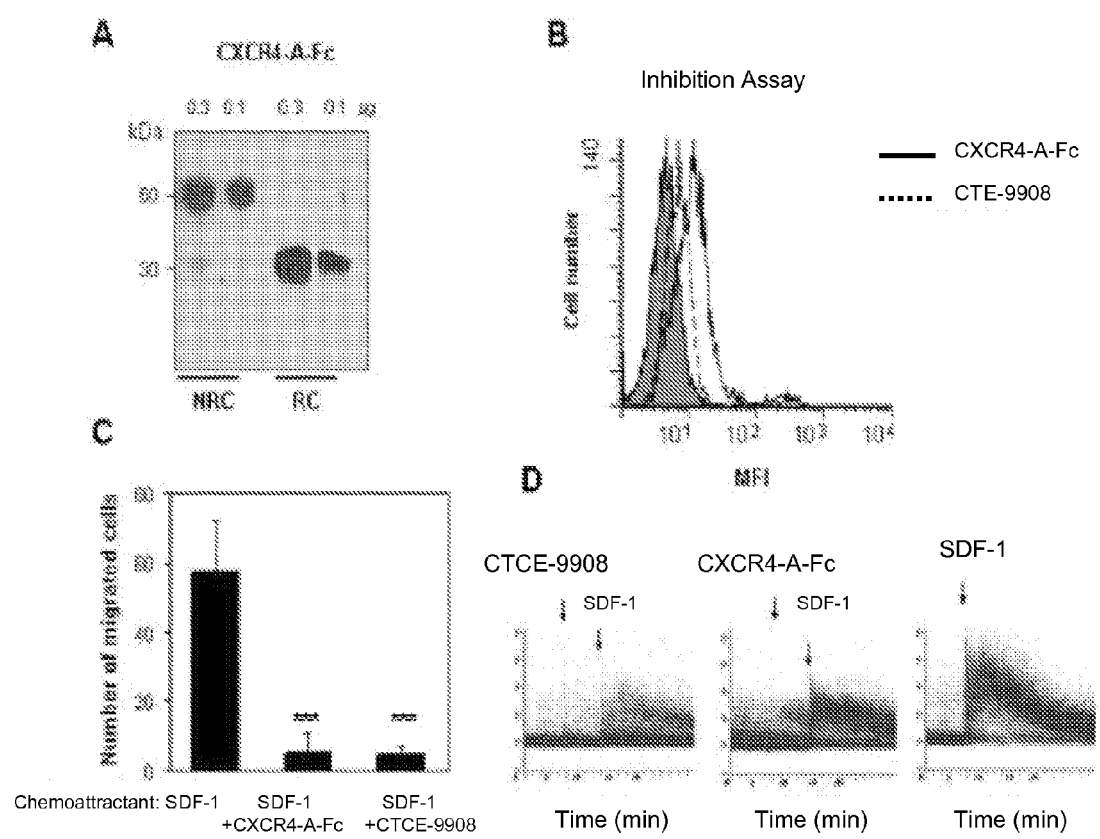
FIG. 9. Characterization of the CXCR4-A-Fc fusion protein and its interaction with CXCR4. A, Western blot of CXCR4-A-Fc isolated from the supernatant of virally-infected cells under non-reducing (NRC) and reducing (RC) conditions. B. Inhibition of CXCR4-A-Fc binding to CXCR4 on SUPT-1 cells by CTCE-9908 peptide. Cells were incubated with biotinylated CXCR4-A-Fc (300 μg/ml) and analyzed for binding with streptavidin-PE. For the inhibition assay, the cells were incubated with CTCE-9908 peptide (100 μg/ml) prior to staining with the fusion protein. Background staining was assessed using an isotype control. C. Inhibition of migration by the fusion protein. 4T1 cells ($5 \times 10^4$) were plated in the upper chamber of a 8 μm transwell system in medium alone or medium containing CXCR4-A-Fc or CTCE-9908 peptide (100 μg/ml). The lower chamber was filled with 1 ml of medium containing SDF-1 (1,000 ng/ml). After 10 h of migration through the transwell membrane, cells were fixed, stained and enumerated in six fields of view to quantify migration. The results are the mean±SD numbers of migrated cells/microscopic field. The numbers of migrating cells in control cultures were subtracted from the experimental values. Data are representative of three experiments. D. Inhibition of SDF-1-induced calcium mobilization by CXCR4-A-FC. Cells ($1 \times 10^6$) were loaded with 10 μM Indo-1 AM for 45 min in dark at 37° C. After a 3 to 5 min measurement of basal fluorescence, CTCE-9908 or CXCR4-A-Fc (300 μg/ml) were added to Indo-1-loaded cells followed by SDF-1 (50 ng/ml). Changes in fluorescence were recorded as a function of time, and were determined by measuring the ratio of 410 nm emission fluorescence (calcium bound to indo-1) to 490 nm emission fluorescence. The 410 and 490 nm emissions and the 410:490 ratio were collected over time (0-5 min) before and after the administration of SDF-1 and inhibitors. Data are representative of two experiments. ***, P<0.0001.

We generated OVV-EGFP (expressing the Enhanced Green Fluorescence Protein used as control) and OVV-CXCR4A-Fc by homologous recombination in CV-1 cells using VSC20 vaccinia virus and the vaccinia shuttle plasmids pSEL-EGFP and pCB023-CXCR4A-Fc, respectively [Mc-Cart, J. A., Ward, J. M., Lee, J., Hu, Y., Alexander, H. R., Libutti, S. K., Moss, B. and Bartlett, D. L., Systemic cancer therapy with a tumor-selective vaccinia virus mutant lacking thymidine kinase and vaccinia growth factor genes. Cancer Res 2001. 61: 8751-8757]. The fusion protein was purified from culture supernatant of OVV-CXCR4A-Fc-infected TK$^-$ cells and analyzed by Western blotting under reducing and nonreducing conditions revealed the fusion protein as a dimer consisted of 28.9 kDa monomers (FIG. 9A). The fusion protein was capable of binding to the CXCR4 receptor expressed on SupT-1 cells and the binding was inhibited by pre-incubation of these cells with CTCE-9908 peptide, indicating that both ligands bind to the same epitope of CXCR4 (FIG. 9B). In vitro migration assay of 4T1 cells in 24-mm diameter chambers with 8.0 μm pore filters revealed that addition of either the CXCR4A-Fc fusion protein or CTCE-9908 peptide (100 μg/ml; AAPPTec LLC, Louisville, Ky.) inhibited by >80% migration of the tumor cells toward SDF1 used at concentration of 1,000 ng/ml (FIG. 9C; $P<0.0001$). Both antagonists were also capable of inhibition of SDF-1-induced calcium mobilization in SUPT-1 cells (FIG. 9D).

Figure 10:
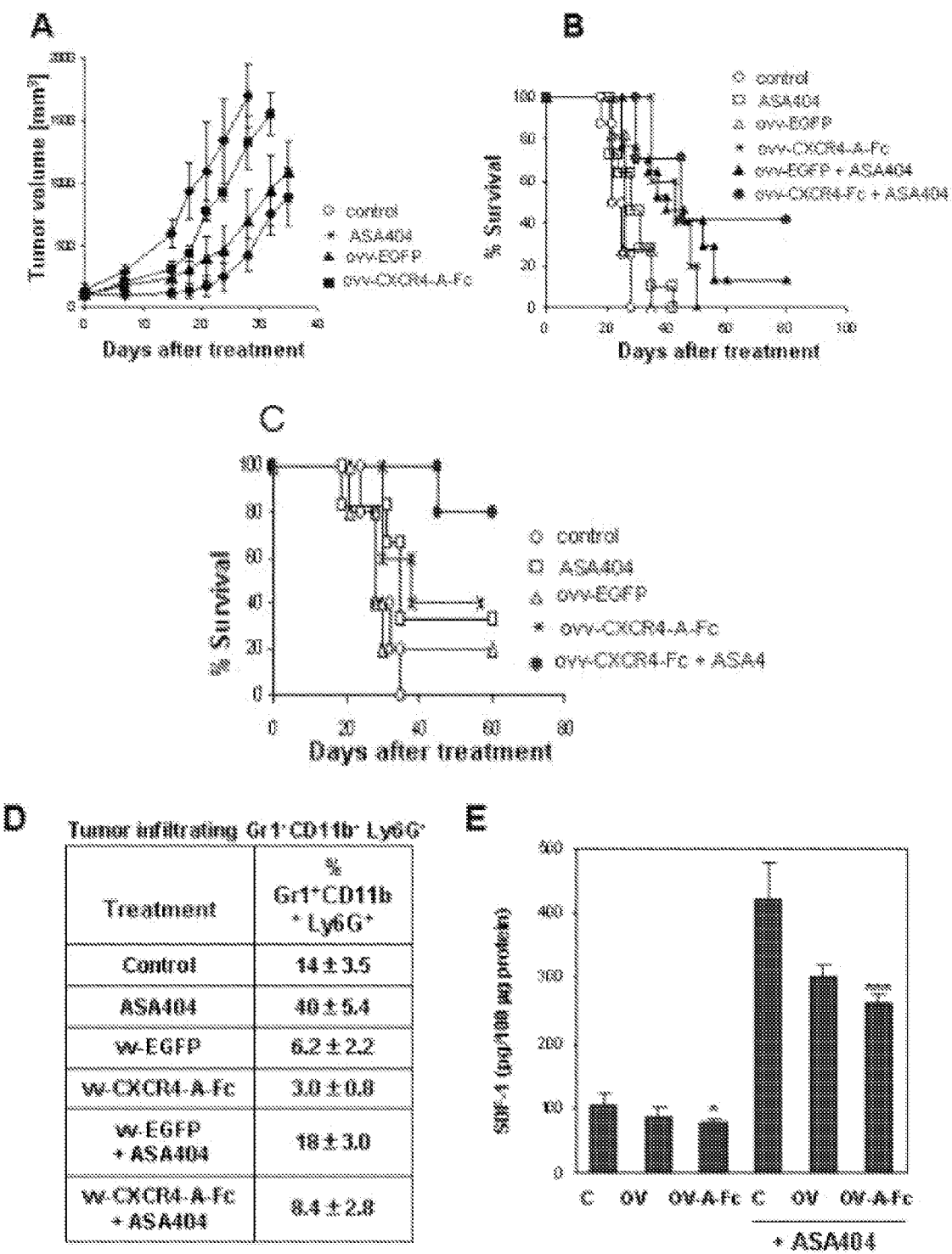
FIG. 10. Inhibition of 4T1 primary and metastatic tumor growth by OVV-CXCR4-A-Fc or ASA404 delivered alone or in combination. A. BALB/c (n=8-12) were inoculated in the thoracic mammary fat pads with $7 \times 10^4$ 4T1 cells. 4T1-bearing mice with tumor volume (V) of 100-150 mm$^3$ were injected i.v. with OVV-EGFP or OVV-CXCR4A-Fc ($10^8$ PFU) or the max. tolerated dose of ASA404 (20 mg/kg). B. Inhibition of 4T1 primary and metastatic tumor growth by OVV-CXCR4-A-Fc or ASA404 delivered alone or in combination. Kaplan-Meier survival plots were prepared and median survival times were determined for tumor-challenged groups of mice. Statistical differences in the survival across groups were assessed using the logrank Mantel-Cox method. C. For the therapy of metastatic disease, 4T1-bearing mice underwent oncolytic virotherapy (V=~200 mm$^3$) alone or in combination with ASA404 and tumors were excised eight days later. Control mice had the primary tumor excised without treatment. Survival was defined as the point at which mice were euthanized due to extensive tumor burden. D. The percentage of MDSCs (Gr1$^+$, CD11b$^+$, Ly6G$^+$) in tumor microenvironment was determined 4 days after the treatment by immunofluoresce staining of single cell suspensions by flow cytometry. E. The levels of SDF-1 in cell lysates prepared from tumors were determined by ELISA assay (*, P<0.05; ***, P<0.0001). Data were presented as arithmetic mean±SD of thee independence experiments.

Inhibition of 4T1 primary and metastatic growth in BALB/c mice. Female BALB/c (n=8-12) were inoculated in the thoracic mammary fat pad with $7 \times 10^4$ 4T1 cells in 50 μl PBS. 4T1-bearing mice with tumor volume of 100-150 mm$^3$ were injected i.v. with OVV-EGFP or OVV-CXCR4A-Fc ($10^8$ PFU) alone or in combination with the max tolerated dose of ASA404 (20 mg/kg) delivered i.p. 24-h after the virus. This time of ASA404 delivery showed the optimal antitumor efficacy compared to animals treated with the drug delivered 4 h before or simultaneous with the virus (not shown). FIG. 10A shows that although monotherapy with OVV-CXCR4-A-Fc or ASA404 significantly inhibited tumor growth ($P<0.05$), tumor-free survival was achieved only in animals treated with the combination therapy (FIG. 10B). Treatment with OVV-EGFP and ASA404 resulted in 13% survival whereas OVV-CXCR4-Fc and ASA404 resulted in 42% tumor-free animals (FIG. 10B). For the therapy of metastatic disease, 4T1-bearing mice (V=~200 mm$^3$) underwent oncolytic virotherapy alone or in combination with ASA404, and tumors were excised eight days later (the time when virus infection was eliminated due to innate and adaptive immunity of the host; data not shown). Control mice had the primary tumor excised without treatment. As shown in FIG. 10C, the highest protection against metastatic disease was observed in animals treated with the combination of OVV-CXCR4-Fc and ASA404 (80% survival). Oncolytic virotherapy or ASA404 treatment alone was less protective. Consistent with changes in the survival profile, the numbers of Gr1$^+$CD11b$^+$ (Ly6G$^+$) MDSCs in 4T1 tumor resected 4 days after treatments differed from those in control animals.

As shown in FIG. 10D, the number of MDSCs (CD11b$^+$ Ly6G$^+$) was ~4-fold lower after OVV-CXCR4-A-Fc treatment compared to control tumors. In contrast, tumors after ASA404 treatment contained the highest accumulation of MDSCs (3-fold increased compared to control). This could be either due to increased migration of MDSCs from periphery due to the-drug-mediated inflammation or inability of these cells to leave the tumor because of vascular damage. The high level of SDF-1 in ASA404-treated tumor and its reduced expression after OVV-CXCR4-A-Fc therapy supports the former possibility (FIG. 10E). Thus, it will be recognized by those skilled in the art that because expression of SDF-1 in cancer-associated fibroblasts present in the tumor microenvironment promotes primary tumor growth by inducing tumor neo-angiogenesis via both paracrine (direct stimulation of tumor CXCR4), and endocrine (recruitment of MDSCs from the bone marrow) mechanisms, targeting CXCR4 according to the method of the invention is expected to be effective in inhibiting malignant tumor growth as well as distant metastasis.

It will be recognized by those skilled in the art from the foregoing that the invention in various embodiments takes advantage of at least three unique reagents, and each one can play a distinct part in inhibiting tumor growth through a direct or indirect mechanism of action. Without intending to be bound by theory, it is considered that destruction of tumor growth is achieved primarily through a cytolytic effect on malignant cells exerted by the oncolytic vaccinia virus and shut-down of tumor vasculature by ASA404, whereas the indirect antitumor effect is achieved by interfering with the cross-communication between tumor and stromal cells, in part, through inflammation and targeting the CXCR4 receptor. We show that this strategy had a profound impact on survival, particularly in a post-surgery metastatic paradigm, of a highly metastatic murine 4T1 breast carcinoma in syngeneic mice. We expect that a combination therapy that attacks both malignant cells and the stromal cells will be more effective and could also elicit long-lasting adaptive immunity to the transformed cells.

The foregoing examples are intended to illustrate the invention. Those skilled in the art will recognized that minor modifications can be made without deviating from the spirit of the invention.

I claim:

1. A method for inhibiting growth of tumor cells in an individual comprising administering to the individual a composition comprising a polynucleotide encoding a protein, wherein the protein encoded by the polynucleotide consists of:
  an immunoglobulin Fc region and only one amino acid sequence of an antagonist peptide of a receptor expressed by the tumor cells, wherein the only one amino acid sequence of the antagonist peptide of the receptor consists of the sequence KGVSLSYR (SEQ ID NO:6);
  such that growth of the tumor cells that express the receptor is inhibited subsequent to the administration, and wherein the polynucleotide encoding the protein is present in a recombinant oncolytic vaccinia virus.

2. The method of claim 1, wherein the Fc is a human IgG1 Fc or human IgG3 Fc.

3. The method of claim 1, wherein the administration is a systemic administration.

4. The method of claim 1, wherein the immunoglobulin Fc does not comprise an antigen binding portion of an immunoglobulin.

* * * * *